United States Patent
Allen, Jr. et al.

(10) Patent No.: US 10,151,055 B2
(45) Date of Patent: Dec. 11, 2018

(54) FIBERS OF POLYMER-WAX COMPOSITIONS

(71) Applicant: The Procter & Gamble Company, Cincinnati, OH (US)

(72) Inventors: William Maxwell Allen, Jr., Liberty Township, OH (US); Eric Bryan Bond, Maineville, OH (US); Isao Noda, Fairfield, OH (US); Ronald Thomas Gorley, Cincinnati, OH (US); Olaf Erik Alexander Isele, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/896,177

(22) Filed: Feb. 14, 2018

(65) Prior Publication Data

US 2018/0171518 A1    Jun. 21, 2018

Related U.S. Application Data

(63) Continuation of application No. 14/920,912, filed on Oct. 23, 2015, now Pat. No. 9,926,653, which is a
(Continued)

(51) Int. Cl.
*D04H 1/4291* (2012.01)
*A61L 15/24* (2006.01)
(Continued)

(52) U.S. Cl.
CPC ............ *D04H 1/4291* (2013.01); *A61L 15/24* (2013.01); *A61L 15/34* (2013.01); *B01J 20/261* (2013.01);
(Continued)

(58) Field of Classification Search
CPC ....... D04H 1/4291; A61L 15/24; A61L 15/34; B01J 20/261; B01J 20/262; B01J 20/264; B01J 20/265; B01J 20/28023; C08K 5/101; C08L 23/06; C08L 23/12; C08L 23/16; C08L 67/02; C08L 67/04; C08L 77/00;
(Continued)

(56) References Cited

U.S. PATENT DOCUMENTS

| 3,093,612 A | 6/1963 | Cox |
| 3,139,412 A | 6/1964 | Sterling |

(Continued)

FOREIGN PATENT DOCUMENTS

| CN | 101291983 | 10/2008 |
| CN | 101955639 A | 1/2011 |

(Continued)

OTHER PUBLICATIONS

12672 Search Report for PCT/US2013/070877 dated Jan. 23, 2014.
(Continued)

*Primary Examiner* — Ling Siu Choi
*Assistant Examiner* — Ronald Grinsted
(74) *Attorney, Agent, or Firm* — George H. Leal

(57) ABSTRACT

Disposable article that include fibers formed from compositions comprising thermoplastic polymers and waxes are disclosed, where the wax is dispersed throughout the thermoplastic polymer.

19 Claims, 9 Drawing Sheets

Related U.S. Application Data continuation of application No. 14/085,642, filed on Nov. 20, 2013, now Pat. No. 9,328,440, which is a continuation of application No. 13/473,925, filed on May 17, 2012.

(60) Provisional application No. 61/488,551, filed on May 20, 2011.

(51) Int. Cl.

| | | |
|---|---|---|
| *A61L 15/34* | (2006.01) | |
| *B01J 20/26* | (2006.01) | |
| *B01J 20/28* | (2006.01) | |
| *C08K 5/101* | (2006.01) | |
| *C08L 23/06* | (2006.01) | |
| *C08L 23/12* | (2006.01) | |
| *C08L 23/16* | (2006.01) | |
| *C08L 67/02* | (2006.01) | |
| *C08L 67/04* | (2006.01) | |
| *C08L 77/00* | (2006.01) | |
| *C08L 91/06* | (2006.01) | |
| *C09D 123/08* | (2006.01) | |
| *C09D 123/10* | (2006.01) | |
| *C09D 167/00* | (2006.01) | |
| *C09D 167/04* | (2006.01) | |
| *C09D 177/04* | (2006.01) | |
| *D01F 6/46* | (2006.01) | |
| *D01F 6/90* | (2006.01) | |
| *D01F 6/92* | (2006.01) | |

(52) U.S. Cl.
CPC ......... *B01J 20/262* (2013.01); *B01J 20/264* (2013.01); *B01J 20/265* (2013.01); *B01J 20/28023* (2013.01); *C08K 5/101* (2013.01); *C08L 23/06* (2013.01); *C08L 23/12* (2013.01); *C08L 23/16* (2013.01); *C08L 67/02* (2013.01); *C08L 67/04* (2013.01); *C08L 77/00* (2013.01); *C08L 91/06* (2013.01); *C09D 123/08* (2013.01); *C09D 123/10* (2013.01); *C09D 167/00* (2013.01); *C09D 167/04* (2013.01); *C09D 177/04* (2013.01); *D01F 6/46* (2013.01); *D01F 6/90* (2013.01); *D01F 6/92* (2013.01); *D10B 2201/01* (2013.01); *D10B 2321/02* (2013.01); *Y10T 428/31801* (2015.04)

(58) Field of Classification Search
CPC ..... C08L 91/06; C09D 123/08; C09D 123/10; C09D 167/00; C09D 167/04; C09D 177/04; D01F 6/46; D01F 6/90; D01F 6/92; Y10T 428/31801; D10B 2201/01; D10B 2321/02
USPC ........................................................ 524/322
See application file for complete search history.

(56) References Cited

U.S. PATENT DOCUMENTS

| | | |
|---|---|---|
| 3,244,785 A | 4/1966 | Hollandsworth |
| 3,338,992 A | 8/1967 | Kinney |
| 3,423,491 A | 1/1969 | McLain |
| 3,704,971 A | 12/1972 | Baird et al. |
| 3,802,817 A | 4/1974 | Matsuki et al. |
| 3,929,678 A | 12/1975 | Laughlin et al. |
| 4,020,230 A | 4/1977 | Mahoney et al. |
| 4,233,014 A | 11/1980 | Kinney |
| 4,259,217 A | 3/1981 | Murphy |
| 4,273,691 A | 6/1981 | MacLaury et al. |
| 4,536,361 A | 8/1985 | Torobin |
| 4,612,148 A | 9/1986 | Motooka et al. |
| 4,666,763 A | 5/1987 | King et al. |
| 4,874,567 A | 10/1989 | Lopatin et al. |
| 5,193,670 A | 3/1993 | Fong |
| 5,498,650 A | 3/1996 | Flexman et al. |
| 5,545,371 A | 8/1996 | Lu |
| 5,667,750 A | 9/1997 | Nohr et al. |
| 5,688,468 A | 11/1997 | Lu |
| 5,885,909 A | 3/1999 | Rudisill et al. |
| 5,925,697 A | 7/1999 | Brauer et al. |
| 5,990,271 A | 11/1999 | Noda |
| RE36,548 E | 2/2000 | Noda |
| 6,231,970 B1 | 5/2001 | Andersen et al. |
| 6,315,806 B1 | 11/2001 | Torobin et al. |
| 6,382,526 B1 | 5/2002 | Reneker et al. |
| 6,520,425 B1 | 2/2003 | Reneker |
| 6,548,431 B1 | 4/2003 | Bansal et al. |
| 6,695,992 B2 | 2/2004 | Reneker |
| 6,746,755 B2 | 6/2004 | Morrison et al. |
| 6,746,766 B2 | 6/2004 | Bond et al. |
| 6,818,295 B2 | 11/2004 | Bond et al. |
| 6,830,810 B2 | 12/2004 | Bond |
| 6,890,872 B2 | 5/2005 | Bond et al. |
| 6,908,292 B2 | 6/2005 | Geus et al. |
| 6,918,750 B2 | 7/2005 | Geus et al. |
| 6,946,506 B2 | 9/2005 | Bond et al. |
| 7,271,209 B2 | 9/2007 | Li et al. |
| 7,402,618 B2 | 7/2008 | Ku |
| 7,476,447 B2 | 1/2009 | Thomas |
| 7,605,208 B2 | 10/2009 | Uosaki et al. |
| 7,628,941 B2 | 12/2009 | Krause et al. |
| 7,666,343 B2 | 2/2010 | Johnson et al. |
| 7,722,347 B2 | 5/2010 | Krause et al. |
| 7,931,457 B2 | 4/2011 | Johnson et al. |
| 8,017,066 B2 | 9/2011 | Hartge |
| 8,026,188 B2 | 9/2011 | Mor |
| 8,153,746 B2 | 4/2012 | Petrovic et al. |
| 8,765,240 B2 | 7/2014 | Grigo et al. |
| 9,328,440 B2 | 5/2016 | Allen, Jr. et al. |
| 2002/0168912 A1 | 11/2002 | Bond et al. |
| 2003/0092343 A1 | 5/2003 | Bond et al. |
| 2003/0108701 A1 | 6/2003 | Bond et al. |
| 2003/0229168 A1 | 12/2003 | Borsinger et al. |
| 2004/0170816 A1 | 9/2004 | Watanabe et al. |
| 2004/0192818 A1 | 9/2004 | Oriani et al. |
| 2006/0008643 A1 | 1/2006 | Lin et al. |
| 2007/0082573 A1 | 4/2007 | Noda et al. |
| 2007/0082982 A1* | 4/2007 | Noda ................. A61L 15/28 524/47 |
| 2007/0100055 A1 | 5/2007 | Uosaki et al. |
| 2008/0045638 A1 | 2/2008 | Chapman et al. |
| 2008/0070994 A1 | 3/2008 | Li et al. |
| 2008/0139070 A1 | 6/2008 | Laura |
| 2008/0179777 A1 | 7/2008 | Wild et al. |
| 2009/0029134 A1 | 1/2009 | Grigo et al. |
| 2010/0330861 A1 | 12/2010 | Mor |
| 2011/0130430 A1 | 6/2011 | Sonneck et al. |
| 2011/0144261 A1 | 6/2011 | Flanigan et al. |
| 2012/0100772 A1 | 4/2012 | Hummelgaard et al. |
| 2012/0204760 A1 | 8/2012 | Puhala et al. |
| 2012/0296036 A1 | 11/2012 | Allen et al. |
| 2012/0321869 A1 | 12/2012 | Allen et al. |
| 2012/0321870 A1 | 12/2012 | Allen et al. |
| 2012/0321871 A1 | 12/2012 | Bond et al. |
| 2013/0004691 A1 | 1/2013 | Allen et al. |
| 2013/0012093 A1 | 1/2013 | Bond et al. |
| 2013/0052901 A1 | 2/2013 | Bond et al. |
| 2013/0053478 A1 | 2/2013 | Bond et al. |
| 2013/0053479 A1 | 2/2013 | Bond et al. |
| 2013/0053480 A1 | 2/2013 | Allen et al. |
| 2013/0089747 A1 | 4/2013 | Allen, Jr. et al. |
| 2013/0091822 A1 | 4/2013 | Siejak et al. |
| 2013/0158169 A1 | 6/2013 | Bond et al. |
| 2014/0005316 A1 | 1/2014 | Thetford et al. |
| 2014/0138584 A1 | 5/2014 | Bond et al. |
| 2014/0142225 A1 | 5/2014 | Bond et al. |
| 2014/0142226 A1 | 5/2014 | Bond et al. |
| 2014/0142233 A1 | 5/2014 | Layman et al. |

(56) References Cited

U.S. PATENT DOCUMENTS

2014/0142234 A1  5/2014  Layman et al.
2016/0040334 A1  2/2016  Allen, Jr. et al.

FOREIGN PATENT DOCUMENTS

| DE | 19542157 A1 | 5/1997 |
|---|---|---|
| EP | 0735089 A2 | 10/1996 |
| EP | 2266514 A1 | 12/2010 |
| FR | 2789690 A1 | 8/2000 |
| GB | 932897 A1 | 7/1963 |
| JP | 1025420 A1 | 1/1998 |
| MY | 143344 A1 | 4/2011 |
| WO | WO199308874 | 5/1993 |
| WO | WO199308876 | 5/1993 |
| WO | WO1998031735 | 10/1999 |
| WO | WO0190230 A1 | 11/2001 |
| WO | WO2004014997 A2 | 2/2004 |
| WO | WO200444287 A1 | 5/2004 |
| WO | WO200444288 A1 | 5/2004 |
| WO | WO200450965 A1 | 6/2004 |
| WO | WO200450966 A1 | 6/2004 |
| WO | WO2010149239 A1 | 12/2010 |

OTHER PUBLICATIONS

13141 Search Report for PCT/US2013/070941 dated Mar. 27, 2014.
Ali, Fathilah et al., "Thermal, mechanical and rheological properties of poly(lactic acid)/epoxidized soybean oil blends", Polymer Bulletin 62, pp. 91-98 (2009).
Alkan, Cemil et al., "Preparation, Thermal Properties and Thermal Reliability of Form-Stable Paraffin/Polypropylene Composite for Thermal Energy Storage", J. Polym Environ (2009) 17:254-258.
Binias, D. et al., "Formation of Polypropylene/Stearic Acid Fibers", Journal of Applied Polymer Science, vol. 125, pp. 1020-1026, published online Dec. 31, 2011 at wileyonlinelibrary.com.
Chang, Kwanho et al., "Phase Inversion in Polylactide/Soybean Oil Blends Compatibilized by Poly(isoprene-b-lactide) Block Copolymers", Applied Materials & Inerfaces, vol. 1, No. 10, pp. 2390-2399 (2009).
Chen, Gang et al., "Formation of Microporous membrane of Isotactic Polypropylene in Dibutyl Phthalate-Soybean Oil via Thermally Induced Phase Separation", Journal of Applied Polymer Science, vol. 105, pp. 2000-2007 (2007).
Devesh, Tripathi, "Practical Guide to Polypropylene", Smithers RAPRA Technology, 2002.
Drexel University, Fiber Spinning—Drexel University Chemical Engineering Department, Feb. 16, 1999.
Jeon, M.Y. et al., "Phase behavior of polymer/diluent/diluent mixtures and their application to control microporous membrane structure", Journal of Membrane Science 300 (2007) pp. 172-181.
Kim, "Effects of Nucleating Agents on Preparation of Polypropylene Hollow Fiber Membranes by Melt Spinning Process", Maromolecular Research, vol. 10, No. 2, 127-134 pgs. (2002).
Kim, Microporous Membrane Formation Via Thermally Induced Phase Separation, Journal of Membrane Science, 64, (1991) 13-29.
Kim, Operation Parameters of Melt Spinning of Polypropylene Hollow Fiber Membranes, Journal of Membrane Science 108 (1995) 25-36, 12 pages.
Krupa, I. et al., "Thermal properties of uncross-linked and cross-linked LLDPE/wax blends", Polymer Degradation and Stability 70 (2000) pp. 111-117.
Krupa, Polypropylene as a Potential Matrix for the Creation of Shape Stabilized Phase Change Materials, European Polymer Journal 43 (2007) 895-907, 13 pages.
Krupa, Thermal Properties of Polypropylene/Wax Blends, Thermochimica Acta 372 (2001) 137-141, 5 pages.
Lloyd, Douglas R. et al., "Microporous membrane formation via thermally-induced phase separation. II. Liquid-liquid phase separataion", Journal of Membrane Science, 64 (1991) pp. 1-11.
Luo, Benzhe et al., "Effects of nucleating agents and extractants on the structure of polypropylene microporous membranes via thermally induced phase separation", Desalination 192 (2006), pp. 142-150.
LyondellBasell Pro-fax PH835 Polypropylene Homopolymer Technical Data Sheet; http://www.matweb.com/search/GetMatisByManufacturer.aspx?navletter=B&man1D=103, 2012.
Matsuyama, Hideto et al., "Effect of Diluents on Membrane Formation via Thermally Induced Phase Separation", Journal of Applied Polymer Science, vol. 82, 2001, pp. 169-177.
Mendes, Ana et al., "Studies on the Experimental Variables Effects on Rhodium Catalyzed Hydroformylation of Unsaturated Fatty Esters and Comparison of [RhH(CO)(PPh3)3] and [RhCI3.3H2O] as Starting Catalytic Precursors", J. Braz. Chem. Soc., vol. 16, No. 6A, 2005, pp. 1124-1129.
Mpanza, Comparison of Different Waxes as Processing Agents for Low-Density Polyethylene, Polymer Testing 25(2006)436-442, 7 pages.
Petricci, Elena et al., "Microwaves make Hydroformylation a Rapid and Easy Process", Organic Letters, 2006, vol. 8, No. 17, pp. 3725-3727.
Science Lab.com—Mineral Oil—Material Safety Data Sheet—Jun. 9, 2012; http://www.sciencelab.com/msds.php?msdslk-9927364.
Spitzer, Volker et al., Identification of a-Parinaric Acid in the Seed Oil of Sebastiana brasiliensis Sprengel (Euphorbiaceae), JAOCS, vol. 73, No. 5 (1996), pp. 569-573.
Tolinski, Additives for Polyolefins, 2009, pp. 158-168.
Wang, Jianli et al., "Rheologoy Behavior of High-Density Polyethylene/ Diluent Blends and Fabrication of Hollow-Fiber Membranes via Thermally Induced Phase Separation", Journal of Applied Polymer Science, vol. 118, 2186-2194 (2010).
Xiaofan, Flow Polymers, Effects of SureFlo® on the Crystallization and Melting Behavior of Semi-Crystalline Polyethylene (PE) and Polypropylene (PP) Systems, Flow Polymers, LLC, 3 pages.
Yoo, Effects of the Diluent Mixing Ratio and Conditions of the Thermally Induced Phase-Separation Process on the Pore Size of Microporous Polyethylene Membranes, Journal of Applied Polymer Science, vol. 108, 3154-3162 (2008).
Yordem, O. Sinan et al., "Reinforcing and Toughening of Polypropylene With Self-Assembled Low Molar Mass Additives", Department of Polymer Science and Engineering, vol. 51(3), pp. 550-558 Mar. 2011.
All Office Actions, U.S. Appl. No. 13/475575, filed May 18, 2012.
All Office Actions, U.S. Appl. No. 13/475,633, filed May 18, 2012.
All Office Actions U.S. Appl. No. 13/475,602, filed May 18, 2012.
All Office Actions U.S. Appl. No. 13/474,662, filed May 17, 2012.
All Office Actions for U.S. Appl. No. 13/473,925, filed May 17, 2012.
All Office Actions for U.S. Appl. No. 13/475,620, filed May 18, 2012.
All Office Actions for U.S. Appl. No. 14/085,642, filed Nov. 20, 2013.
All Office Actions for U.S. Appl. No. 14/920,912, filed Oct. 23, 2015.

* cited by examiner

Table 1

| | | | Ratio | | Twin-Screw Temperature Profile (°C) | | | | | | | | | Poly Temp (°C) | Wax Temp (°C) | Screw RPM | Screw Type | Torque (%) |
|---|---|---|---|---|---|---|---|---|---|---|---|---|---|---|---|---|---|---|
| | Polymer | Wax | Poly-mer | Wax | Z1 | Z2 | Z3 | Z4 | Z5 | Z6 | Z7 | Z8 | Z9 | Die | | | | | |
| 1 | PH-835 | HSBO | 90 | 10 | 40 | 160 | 180 | 200 | 200 | 200 | 210 | 210 | 210 | 170 | 216 | 80 | 400 | Intensive | 56 |
| 2 | PH-835 | HSBO | 80 | 20 | 40 | 160 | 180 | 200 | 200 | 200 | 210 | 210 | 210 | 170 | 216 | 80 | 400 | Intensive | 43 |
| 3 | PH-835 | HSBO | 70 | 30 | 40 | 160 | 180 | 200 | 200 | 200 | 210 | 210 | 210 | 170 | 217 | 80 | 400 | Intensive | 30 |
| 4 | Achieve 3854 | HSBO | 90 | 10 | 40 | 160 | 180 | 200 | 200 | 200 | 210 | 210 | 210 | 170 | 220 | 80 | 500 | Intensive | 50 |
| 5 | Achieve 3854 | HSBO | 80 | 20 | 40 | 160 | 180 | 200 | 200 | 200 | 210 | 210 | 210 | 170 | 215 | 80 | 500 | Intensive | 41 |
| 6 | Achieve 3854 | HSBO | 70 | 30 | 40 | 160 | 180 | 200 | 200 | 200 | 210 | 210 | 210 | 170 | 218 | 80 | 500 | Intensive | 30 |
| 7 | PH-835 | PHSBO | 90 | 10 | 40 | 160 | 180 | 200 | 200 | 200 | 210 | 210 | 210 | 170 | 202 | 80 | 400 | Intensive | 60 |
| 8 | PH-835 | PHSBO | 80 | 20 | 40 | 160 | 180 | 200 | 200 | 200 | 210 | 210 | 210 | 170 | 199 | 80 | 400 | Intensive | 44 |
| 9 | PH-835 | PHSBO | 70 | 30 | 40 | 160 | 180 | 200 | 200 | 200 | 210 | 210 | 210 | 170 | 201 | 80 | 400 | Intensive | 39 |
| 10 | Achieve 3854 | PHSBO | 90 | 10 | 40 | 160 | 180 | 200 | 200 | 200 | 210 | 210 | 210 | 170 | 204 | 80 | 500 | Intensive | 5 |
| 11 | Achieve 3854 | PHSBO | 80 | 20 | 40 | 160 | 180 | 200 | 200 | 200 | 210 | 210 | 210 | 170 | 202 | 80 | 500 | Intensive | 44 |
| 12 | Achieve 3854 | PHSBO | 70 | 30 | 40 | 160 | 180 | 200 | 200 | 200 | 210 | 210 | 210 | 170 | 205 | 80 | 500 | Intensive | 38 |
| 13 | PH-835 | HSBO | 90 | 10 | 40 | 160 | 180 | 240 | 240 | 240 | 240 | 210 | 210 | 170 | NR | 80 | 400 | High | NR |
| 14 | PH-835 | HSBO | 80 | 20 | 40 | 160 | 180 | 240 | 240 | 240 | 240 | 210 | 210 | 170 | 176 | 80 | 400 | High | 45 |
| 15 | PH-835 | HSBO | 70 | 30 | 40 | 160 | 180 | 240 | 240 | 240 | 240 | 210 | 210 | 170 | 173 | 80 | 400 | High | 37 |
| 16 | PH-835 | HSBO | 60 | 40 | 40 | 160 | 180 | 240 | 240 | 240 | 240 | 210 | 210 | 170 | 176 | 80 | 400 | High | 31 |
| 17 | Total 8650 | HSBO | 60 | 40 | 40 | 160 | 180 | 240 | 240 | 240 | 240 | 210 | 210 | 170 | 178 | 80 | 600 | High | 27 |

Figure 4

| # | Polymer | Wax | Ratio | | Twin-Screw Temperature Profile (°C) | | | | | | | | | | Poly Temp (°C) | Wax Temp (°C) | Screw RPM | Screw Type | Torque (%) |
|---|---|---|---|---|---|---|---|---|---|---|---|---|---|---|---|---|---|---|---|
| | | | Polymer | Wax | Z1 | Z2 | Z3 | Z4 | Z5 | Z6 | Z7 | Z8 | Z9 | Die | | | | | |
| 18 | PH-835 | HSBO | 60 | 40 | 40 | 160 | 180 | 260 | 260 | 260 | 260 | 210 | 210 | 170 | 176 | 80 | 400 | High | 25 |
| 19 | Total 8650 | HSBO | 60 | 40 | 40 | 160 | 180 | 260 | 260 | 260 | 260 | 210 | 210 | 170 | 179 | 80 | 600 | High | 27 |
| 20 | Total 8650 | HSBO | 90 | 10 | 40 | 160 | 180 | 200 | 200 | 200 | 210 | 210 | 210 | 170 | 184 | 80 | 600 | High | 51 |
| 21 | Total 8650 | HSBO | 80 | 20 | 40 | 160 | 180 | 200 | 200 | 200 | 210 | 210 | 210 | 170 | 185 | 80 | 600 | High | 41 |
| 22 | Total 8650 | HSBO | 70 | 30 | 40 | 160 | 180 | 200 | 200 | 200 | 210 | 210 | 210 | 170 | 182 | 80 | 600 | High | 32 |
| 23 | PH-835 | PHPKO | 70 | 30 | 40 | 160 | 180 | 200 | 200 | 200 | 210 | 210 | 210 | 170 | 203 | 80 | 400 | High | 43 |
| 24 | Danimer 27510 | HSBO | 95 | 5 | 40 | 170 | 180 | 180 | 180 | 180 | 180 | 180 | 180 | 170 | 164 | 80 | 400 | High | 27 |
| 25 | Danimer 27510 | HSBO | 93 | 7 | 40 | 170 | 180 | 180 | 180 | 180 | 180 | 180 | 180 | 170 | 165 | 80 | 400 | High | 26 |
| 26 | Danimer 27510 | HSBO | 90 | 10 | 40 | 170 | 180 | 180 | 180 | 180 | 180 | 180 | 180 | 170 | 167 | 80 | 400 | High | 25 |
| 27 | Danimer 27510 | HSBO | 85 | 15 | 40 | 170 | 180 | 180 | 180 | 180 | 180 | 180 | 180 | 170 | NR | 80 | 400 | High | NR |
| 28 | Aspun 6811A | HSBO | 90 | 10 | 40 | 160 | 180 | 190 | 190 | 190 | 190 | 190 | 190 | 170 | 173 | 80 | 500 | High | 55 |
| 29 | Aspun 6811A | HSBO | 80 | 20 | 40 | 160 | 180 | 190 | 190 | 190 | 190 | 190 | 190 | 170 | 170 | 80 | 500 | High | 46 |
| 30 | Aspun 6811A | HSBO | 70 | 30 | 40 | 160 | 180 | 190 | 190 | 190 | 190 | 190 | 190 | 170 | 170 | 80 | 500 | High | 39 |
| 31 | Aspun 6811A | HSBO | 60 | 40 | 40 | 160 | 180 | 190 | 190 | 190 | 190 | 190 | 190 | 170 | 171 | 80 | 500 | High | 30 |
| 32 | Aspun 6811A | HSBO | 50 | 50 | 40 | 160 | 180 | 190 | 190 | 190 | 190 | 190 | 190 | 170 | 173 | 80 | 500 | High | 23 |

Figure 5

| | Polymer | Wax | Ratio | | Twin-Screw Temperature Profile (°C) | | | | | | | | | | Poly Temp (°C) | Wax Temp (°C) | Screw RPM | Screw Type | Torque (%) |
|---|---|---|---|---|---|---|---|---|---|---|---|---|---|---|---|---|---|---|---|
| | | | Polymer | Wax | Z1 | Z2 | Z3 | Z4 | Z5 | Z6 | Z7 | Z8 | Z9 | Die | | | | | |
| 33 | Natureworks 4032D | HSBO | 95 | 5 | 40 | 160 | 180 | 190 | 190 | 190 | 190 | 190 | 190 | 170 | 175 | 80 | 600 | High | 47 |
| 34 | Natureworks 4032D | HSBO | 90 | 10 | 40 | 160 | 180 | 190 | 190 | 190 | 190 | 190 | 190 | 170 | NR | 80 | 500 | High | NR |
| 35 | Ultramid B27 | HSBO | 90 | 10 | 40 | 220 | 240 | 250 | 260 | 270 | 270 | 260 | 250 | 240 | 238 | 80 | 600 | High | 47 |
| 36 | Ultramid B27 | HSBO | 85 | 15 | 40 | 220 | 240 | 250 | 260 | 270 | 270 | 260 | 250 | 240 | NR | 80 | 600 | High | NR |
| 37 | Ultramid B27 | HSBO | 80 | 20 | 40 | 220 | 240 | 250 | 260 | 270 | 270 | 260 | 250 | 240 | NR | 80 | 600 | High | NR |
| 38 | Eastman 9921 | HSBO | 95 | 5 | 40 | 220 | 260 | 270 | 290 | 290 | 290 | 290 | 280 | 250 | 262 | 80 | 400 | High | 59 |
| 39 | Eastman 9921 | HSBO | 92 | 8 | 40 | 220 | 260 | 270 | 290 | 290 | 290 | 290 | 280 | 250 | 264 | 80 | 600 | High | 61 |
| 40 | Eastman 9921 | HSBO | 90 | 10 | 40 | 220 | 260 | 270 | 290 | 290 | 290 | 290 | 280 | 250 | 264 | 80 | 600 | High | 59 |
| 41 | Eastman 9921 | HSBO | 85 | 15 | 40 | 220 | 260 | 270 | 290 | 290 | 290 | 290 | 280 | 250 | 264 | 80 | 600 | High | 59 |
| 42 | PH-835 | HSBO | 70 | 30 | 40 | 160 | 180 | 240 | 240 | 240 | 240 | 210 | 210 | 170 | 174 | 80 | 400 | High | 28 |
| 43 | PH-835 | HSBO | 70 | 30 | 40 | 160 | 180 | 240 | 240 | 240 | 240 | 210 | 210 | 170 | 174 | 80 | 400 | High | 28 |
| 44 | CP-360H | HSBO | 90 | 10 | 40 | 160 | 180 | 200 | 200 | 200 | 210 | 210 | 210 | 170 | 172 | 80 | 500 | High | 63 |
| 45 | CP-360H | HSBO | 85 | 15 | 40 | 160 | 180 | 200 | 200 | 200 | 210 | 210 | 210 | 170 | 170 | 80 | 500 | High | 57 |
| 46 | CP-360H | HSBO | 80 | 20 | 40 | 160 | 180 | 200 | 200 | 200 | 210 | 210 | 210 | 170 | 171 | 80 | 500 | High | 52 |

Figure 6

Table 2

| Examples | Sheath Material | Core Material | Sheath Ratio | Core Ratio | Sheath Extruder Z1 | Z2 | Z3 | Z4 | Transfer line | Core Extruder Z1 | Z2 | Z3 | Z4 | Transfer line | Beam Spinpack | Final Diameter (micron) |
|---|---|---|---|---|---|---|---|---|---|---|---|---|---|---|---|---|
| PH-835 | PH-835 | PH-835 | 30 | 70 | 180 | 200 | 220 | 230 | 230 | 180 | 200 | 220 | 230 | 230 | 230 | 17 |
| CP360H | CP360H | CP360H | 30 | 70 | 180 | 200 | 220 | 230 | 230 | 180 | 200 | 220 | 230 | 230 | 230 | 18 |
| 47 | PH-835 | Example 1 | 30 | 70 | 180 | 200 | 220 | 230 | 230 | 180 | 200 | 220 | 230 | 230 | 230 | 16 |
| 48 | Example 1 | Example 1 | 30 | 70 | 180 | 200 | 220 | 230 | 230 | 180 | 200 | 220 | 230 | 230 | 230 | 15* |
| 49 | PH-835 | Example 2 | 30 | 70 | 180 | 200 | 220 | 230 | 230 | 180 | 200 | 220 | 230 | 230 | 230 | 16 |
| 50 | Example 2 | Example 2 | 30 | 70 | 180 | 200 | 220 | 230 | 230 | 180 | 200 | 220 | 230 | 230 | 230 | 15* |
| 51 | PH-835 | Example 3 | 30 | 70 | 180 | 200 | 220 | 230 | 230 | 180 | 200 | 220 | 230 | 230 | 230 | 15 |
| 52 | Example 3 | Example 3 | 30 | 70 | 180 | 200 | 220 | 230 | 230 | 180 | 200 | 220 | 230 | 230 | 230 | 15* |
| 53 | PH-835 | Example 4 | 30 | 70 | 180 | 200 | 220 | 230 | 230 | 180 | 200 | 220 | 230 | 230 | 230 | 17 |
| 54 | Example 4 | Example 4 | 30 | 70 | 180 | 200 | 220 | 230 | 230 | 180 | 200 | 220 | 230 | 230 | 230 | 15* |
| 55 | PH-835 | Example 5 | 30 | 70 | 180 | 200 | 220 | 230 | 230 | 180 | 200 | 220 | 230 | 230 | 230 | 17 |
| 56 | Example 5 | Example 5 | 30 | 70 | 180 | 200 | 220 | 230 | 230 | 180 | 200 | 220 | 230 | 230 | 230 | 15* |
| 57 | PH-835 | Example 24 | 30 | 70 | 180 | 200 | 220 | 230 | 230 | 180 | 200 | 220 | 230 | 230 | 230 | 17 |
| 58 | Example 24 | Example 24 | 30 | 70 | 180 | 200 | 220 | 230 | 230 | 180 | 200 | 220 | 230 | 230 | 230 | 16* |
| 59 | PH-835 | Example 25 | 30 | 70 | 180 | 200 | 220 | 230 | 230 | 180 | 200 | 220 | 230 | 230 | 230 | 18 |
| 60 | Example 25 | Example 25 | 30 | 70 | 180 | 200 | 220 | 230 | 230 | 180 | 200 | 220 | 230 | 230 | 230 | 16 |
| 8650 | 8650 | 8650 | 30 | 70 | 180 | 200 | 220 | 230 | 230 | 180 | 200 | 220 | 230 | 230 | 230 | 20 |
| 61 | Example 11 | Example 11 | 30 | 70 | 180 | 200 | 220 | 230 | 230 | 180 | 200 | 220 | 230 | 230 | 230 | 15 |
| 62 | PH-835 | Example 8 | 30 | 70 | 180 | 200 | 220 | 230 | 230 | 180 | 200 | 220 | 230 | 230 | 230 | 15 |

Figure 7

| | | | | | | | | | | | |
|---|---|---|---|---|---|---|---|---|---|---|---|
| 63 | Example 47 | 30 | 70 | 180 | 200 | 220 | 230 | 180 | 200 | 220 | 230 | 230 | 16 |
| 64 | Example 48 | 30 | 70 | 180 | 200 | 220 | 230 | 180 | 200 | 220 | 230 | 230 | 16 |
| 65 | Example 49 | 30 | 70 | 180 | 200 | 220 | 230 | 180 | 200 | 220 | 230 | 230 | 15 |

*denotes could not reach fiber spinning failure at maximum draw down pressure

Figure 8

Table 3

| Example | Sheath Material | Core Material | Fiber Example | Temperature (oC) Engraved Roll | Temperature (oC) Smooth Roll | Average Basis Wt (gsm) | MD Tensile Peak Ld (N) | St. Dev | MD Elongation (%) | St. Dev | CD Tensile Strength Peak Ld (N) | St. Dev | CD Elongation (%) | St. Dev |
|---|---|---|---|---|---|---|---|---|---|---|---|---|---|---|
| 66 | CP360H | CP360H | CP360H | 115 | 110 | 19.9 | 25.7 | 1.5 | 19 | 2 | 13.1 | 1.9 | 28 | 4 |
| 67 | CP360H | CP360H | CP360H | 120 | 115 | 19.6 | 26.8 | 2.6 | 22 | 3 | 13.2 | 1.9 | 27 | 4 |
| 68 | CP360H | CP360H | CP360H | 125 | 120 | 20.3 | 31 | 1.7 | 26 | 3 | 14.5 | 2.6 | 30 | 6 |
| 69 | CP360H | CP360H | CP360H | 130 | 125 | 19.5 | 37 | 1.7 | 34 | 3 | 16.1 | 2.3 | 35 | 4 |
| 70 | CP360H | CP360H | CP360H | 135 | 130 | 20.4 | 41.4 | 1.8 | 40 | 3 | 19.3 | 1.3 | 42 | 3 |
| 71 | CP360H | CP360H | CP360H | 140 | 135 | 20.5 | 46.1 | 3.8 | 42 | 7 | 23.8 | 2.4 | 52 | 3 |
| 72 | CP360H | CP360H | CP360H | 145 | 140 | 19.7 | 41.2 | 4.9 | 32 | 8 | 21.9 | 3.5 | 49 | 5 |
| 73 | CP360H | CP360H | CP360H | 150 | 145 | 20.3 | 34.4 | 5.6 | 19 | 5 | 22.9 | 2.9 | 43 | 5 |
| 74 | CP360H | CP360H | CP360H | 155 | 150 | 21 | 25.2 | 2.5 | 10 | 2 | 13.6 | 1.5 | 27 | 3 |
| 75 | CP360H | CP360H | CP360H | 160 | 155 | 20.5 | 17.9 | 3.8 | 6 | 1 | 10.3 | 1.9 | 20 | 3 |
| 76 | Example 47 | Example 47 | Example 66 | 115 | 110 | 22.3 | 19.6 | 1.6 | 18 | 2 | 7 | 1 | 25 | 5 |
| 77 | Example 47 | Example 47 | Example 66 | 120 | 115 | 21.7 | 21.7 | 1.3 | 21 | 2 | 8 | 1 | 28 | 3 |
| 78 | Example 47 | Example 47 | Example 66 | 125 | 120 | 21.4 | 24.3 | 1.9 | 26 | 3 | 10 | 1 | 32 | 4 |
| 79 | Example 47 | Example 47 | Example 66 | 130 | 125 | 21.8 | 28.4 | 2 | 36 | 4 | 13 | 2 | 44 | 4 |
| 80 | Example 47 | Example 47 | Example 66 | 135 | 130 | 21.6 | 38.4 | 2.8 | 51 | 7 | 17 | 2 | 58 | 8 |
| 81 | Example 47 | Example 47 | Example 66 | 140 | 135 | 22.1 | 42.5 | 3.3 | 55 | 7 | 21 | 2 | 62 | 5 |
| 82 | Example 47 | Example 47 | Example 66 | 145 | 140 | 22.5 | 43.1 | 2.9 | 48 | 8 | 25 | 2 | 73 | 9 |
| 83 | Example 47 | Example 47 | Example 66 | 150 | 145 | 22.9 | 38.4 | 3.1 | 31 | 5 | 23 | 3 | 52 | 6 |
| 84 | Example 47 | Example 47 | Example 66 | 155 | 150 | 22.5 | 30.6 | 3 | 17 | 3 | 16 | 2 | 28 | 4 |
| 85 | Example 47 | Example 47 | Example 66 | 160 | 155 | 21.9 | 25.7 | 1.7 | 11 | 2 | 16 | 1 | 28 | 5 |
| 86 | Example 47 | Example 47 | Example 66 | 165 | 160 | 23.6 | 22.6 | 1.9 | 9 | 2 | 12 | 2 | 11 | 2 |
| 87 | Example 48 | Example 48 | Example 67 | 115 | 110 | 23.7 | 26.9 | 2 | 26 | 2 | 9 | 1 | 35 | 3 |
| 88 | Example 48 | Example 48 | Example 67 | 120 | 115 | 22.2 | 27.5 | 1.8 | 31 | 3 | 10 | 1 | 34 | 3 |

Row groupings (left margin): Examples 66–75: CP360H; Examples 76–86: 10% SBO; Examples 87–88: 15% SBO.

Figure 9

| | | | | | | | | | | | | | | |
|---|---|---|---|---|---|---|---|---|---|---|---|---|---|---|
| 89 | Example 48 | Example 48 | Example 67 | 125 | 120 | 23.3 | 32.4 | 1.1 | 36 | 2 | 13 | 1 | 47 | 5 |
| 90 | Example 48 | Example 48 | Example 67 | 130 | 125 | 22.6 | 37.2 | 1.5 | 43 | 2 | 15 | 1 | 55 | 6 |
| 91 | Example 48 | Example 48 | Example 67 | 135 | 130 | 22.7 | 42.4 | 2.5 | 55 | 7 | 18 | 2 | 69 | 8 |
| 92 | Example 48 | Example 48 | Example 67 | 140 | 135 | 23 | 45.3 | 2.7 | 52 | 7 | 21 | 2 | 78 | 9 |
| 93 | Example 48 | Example 48 | Example 67 | 145 | 140 | 24.2 | 41.9 | 3.7 | 40 | 8 | 24 | 3 | 76 | 6 |
| 94 | Example 48 | Example 48 | Example 67 | 150 | 145 | 26.1 | 38.3 | 1.7 | 25 | 3 | 20 | 2 | 51 | 7 |
| 95 | Example 49 | Example 49 | Example 68 | 115 | 110 | 22.2 | 22.8 | 1.6 | 31 | 3 | 7 | 1 | 42 | 4 |
| 96 | Example 49 | Example 49 | Example 68 | 120 | 115 | 21.9 | 23.8 | 1.3 | 34 | 4 | 8 | 1 | 45 | 6 |
| 97 | Example 49 | Example 49 | Example 68 | 125 | 120 | 21.4 | 26.8 | 1.3 | 39 | 3 | 11 | 1 | 55 | 8 |
| 98 | Example 49 | Example 49 | Example 68 | 130 | 125 | 21.1 | 28.4 | 1.2 | 44 | 4 | 13 | 1 | 68 | 9 |
| 99 | Example 49 | Example 49 | Example 68 | 135 | 130 | 20.9 | 30 | 2.2 | 44 | 5 | 15 | 2 | 82 | 15 |
| 100 | Example 49 | Example 49 | Example 68 | 140 | 135 | 22.4 | 31.6 | 2.3 | 43 | 7 | 18 | 2 | 92 | 15 |
| 101 | Example 49 | Example 49 | Example 68 | 145 | 140 | 21.9 | 30.1 | 3.1 | 35 | 7 | 16 | 6 | 81 | 14 |
| 102 | Example 49 | Example 49 | Example 68 | 150 | 145 | 21 | 26.2 | 1.2 | 23 | 4 | 15 | 1 | 59 | 7 |
| 103 | Example 49 | Example 49 | Example 68 | 155 | 150 | 22.2 | 23.3 | 0.8 | 15 | 3 | 13 | 2 | 43 | 8 |
| 104 | Example 49 | Example 49 | Example 68 | 160 | 155 | 22.7 | 24 | 1.7 | 14 | 2 | 12 | 1 | 36 | 5 |
| 105 | Example 49 | Example 49 | Example 68 | 165 | 160 | 23.9 | 17.9 | 1.4 | 7 | 2 | 9 | 1 | 29 | 6 |

20% SBO

Figure 10

FIBERS OF POLYMER-WAX COMPOSITIONS

FIELD OF THE INVENTION

In one aspect, the invention relates to fibers formed from compositions comprising intimate admixtures of thermoplastic polymers and waxes. Another aspect of the invention also relates to methods of making these compositions.

BACKGROUND OF THE INVENTION

Thermoplastic polymers are used in a wide variety of applications. However, thermoplastic polymers, such as polypropylene and polyethylene pose additional challenges compared to other polymer species, especially with respect to formation of, for example, fibers. This is because the material and processing requirements for production of fibers are much more stringent than for producing other forms, for example, films. For the production of fibers, polymer melt flow characteristics are more demanding on the material's physical and rheological properties vs other polymer processing methods. Also, the local extensional rate and shear rate are much greater in fiber production than other processes and, for spinning very fine fibers, small defects, slight inconsistencies, or phase incompatibilities in the melt are not acceptable for a commercially viable process. Moreover, high molecular weight thermoplastic polymers cannot be easily or effectively spun into fine fibers. Given their availability and potential strength improvement, it would be desirable to provide a way to easily and effectively spin such high molecular weight polymers.

Most thermoplastic polymers, such as polyethylene, polypropylene, and polyethylene terephthalate, are derived from monomers (e.g., ethylene, propylene, and terephthalic acid, respectively) that are obtained from non-renewable, fossil-based resources (e.g., petroleum, natural gas, and coal). Thus, the price and availability of these resources ultimately have a significant impact on the price of these polymers. As the worldwide price of these resources escalates, so does the price of materials made from these polymers. Furthermore, many consumers display an aversion to purchasing products that are derived solely from petrochemicals, which are non-renewable fossil based resources. Other consumers may have adverse perceptions about products derived from petrochemicals as being "unnatural" or not environmentally friendly.

Thermoplastic polymers are often incompatible with, or have poor miscibility with additives (e.g., waxes, pigments, organic dyes, perfumes, etc.) that might otherwise contribute to a reduced consumption of these polymers in the manufacture of downstream articles. Heretofore, the art has not effectively addressed how to reduce the amount of thermoplastic polymers derived from non-renewable, fossil-based resources in the manufacture of common articles employing these polymers. Accordingly, it would be desirable to address this deficiency. Existing art has combined polypropylene with additives, with polypropylene as the minor component to form cellular structures. These cellular structures are the purpose behind including renewable materials that are later removed or extracted after the structure is formed. U.S. Pat. No. 3,093,612 describes the combination of polypropylene with various fatty acids where the fatty acid is removed. The scientific paper *J. Apply. Polym. Sci* 82 (1) pp. 169-177 (2001) discloses use of diluents on polypropylene for thermally induced phase separation to produce an open and large cellular structure but at low polymer ratio, where the diluent is subsequently removed from the final structure. The scientific paper *J. Apply. Polym. Sci* 105 (4) pp. 2000-2007 (2007) produces microporous membranes via thermally induced phase separation with dibutyl phthalate and soy bean oil mixtures, with a minor component of polypropylene. The diluent is removed in the final structure. The scientific paper *Journal of Membrane Science* 108 (1-2) pp. 25-36 (1995) produces hollow fiber microporous membranes using soy bean oil and polypropylene mixtures, with a minor component of polypropylene and using thermally induced phase separation to produce the desired membrane structure. The diluent is removed in the final structure. In all of these cases, the diluent as described is removed to produce the final structure. These structures before the diluent is removed are oily with excessive amounts of diluent to produce very open microporous structures with pore sizes >10 µm.

There have been many attempts to make nonwoven articles. However, because of costs, the difficultly in processing, and end-use properties, there are only a limited number of options. Useful fibers for nonwoven articles are difficult to produce and pose additional challenges compared to films and laminates. This is because the material and processing characteristics for fibers is much more stringent than for producing films, blow-molding articles, and injection-molding articles. For the production of fibers, the processing time during structure formation is typically much shorter and flow characteristics are more demanding on the material's physical and rheological characteristics. The local strain rate and shear rate are much greater in fiber production than other processes. Additionally, a homogeneous composition is required for fiber spinning. For spinning very fine fibers, small defects, slight inconsistencies, or non-homogeneity in the melt are not acceptable for a commercially viable process. The more attenuated the fibers, the more critical the processing conditions and selection of materials.

Thus, a need exists for fibers from compositions of thermoplastic polymers that allow for use of higher molecular weight and/or decreased non-renewable resource based materials, and/or incorporation of further additives, such as perfumes and dyes. A still further need is for fibers from compositions that leave the additive present to deliver renewable materials in the final product and that can also enable the addition of further additives into the final structure, such as dyes and perfumes, for example.

SUMMARY OF THE INVENTION

In one aspect, the invention is directed to fibers produced by melt spinning compositions comprising an intimate admixture of a thermoplastic polymer and a wax having a melting point greater than 25° C. The wax can have a melting point that is lower than the melting temperature of the thermoplastic polymer. The composition can be in the form of pellets produced to be used as-is or for storage for future use, for example to make fibers. Optionally, the composition can be further processed into the final usable form, such as fibers, films and molded articles. The fibers can have a diameter of less than 200 µm. The fibers can be monocomponent or bicomponent, discrete and/or continuous, in addition to being hollow, round, and/or shaped. The fiber can be thermally bondable.

The thermoplastic polymer can comprise a polyolefin, a polyester, a polyamide, copolymers thereof, or combinations thereof. The thermoplastic polymer can be selected from the group consisting of polypropylene, polyethylene, polypropylene co-polymer, polyethylene co-polymer, polyethylene terephthalate, polybutylene terephthalate, polylactic acid, polyhydroxyalkanoates, polyamide-6, polyamide-6,6, and combinations thereof. Polypropylene having a melt flow index of greater than 0.5 g/10 min or of greater than 10 g/10 min can be used. The polypropylene can have a weight average molecular weight of about 20 kDa to about 700 kDa. The thermoplastic polymer can be derived from a renewable bio-based feed stock origin, such as bio polyethylene or bio polypropylene, and/or can be recycled source, such as post consumer use.

The wax can be present in the composition in an amount of about 1 wt % to about 20 wt %, about 2 wt % to about 15 wt %, or about 3 wt % to about 10 wt % based upon the total weight of the composition. The wax can comprise a lipid, which can be selected from the group consisting of a monoglyceride, diglyceride, triglyceride, fatty acid, fatty alcohol, esterified fatty acid, epoxidized lipid, maleated lipid, hydrogenated lipid, alkyd resin derived from a lipid, sucrose polyester, or combinations thereof. The wax can comprise a mineral wax, such as a linear alkane, a branched alkane, or combinations thereof. Specific examples of mineral wax are paraffin and petrolatum. The wax can be selected from the group consisting of hydrogenated soy bean oil, partially hydrogenated soy bean oil, epoxidized soy bean oil, maleated soy bean oil, tristearin, tripalmitin, 1,2-dipalmitoolein, 1,3-dipalmitoolein, 1-palmito-3-stearo-2-olein, 1-palmito-2-stearo-3-olein, 2-palmito-1-stearo-3-olein, 1,2-dipalmitolinolein, 1,2-distearo-olein, 1,3-distearo-olein, trimyristin, trilaurin, capric acid, caproic acid, caprylic acid, lauric acid, myristic acid, palmitic acid, stearic acid, and combinations thereof. The wax can be selected from the group consisting of a hydrogenated plant oil, a partially hydrogenated plant oil, an epoxidized plant oil, a maleated plant oil. Specific examples of such plant oils include soy bean oil, corn oil, canola oil, and palm kernel oil.

The wax can be dispersed within the thermoplastic polymer such that the wax has a droplet size of less than 2 µm, less than 1 µm, or less than 500 nm within the thermoplastic polymer. The wax can be a renewable material.

The compositions disclosed herein can further comprise an additive. The additive can be oil soluble or oil dispersible. Examples of additives include perfume, dye, pigment, nucleating agent, clarifying agent, anti-microbial agent, surfactant, nanoparticle, antistatic agent, filler, or combination thereof.

In another aspect, provided is a method of making a composition as disclosed herein, the method comprising a) mixing the thermoplastic polymer, in a molten state, with the wax, also in the molten state, to form the admixture; and b) cooling the admixture to a temperature at or less than the solidification temperature of the thermoplastic polymer in 10 seconds or less to form the composition. The method of making a composition can comprise a) melting a thermoplastic polymer to form a molten thermoplastic polymer; b) mixing the molten thermoplastic polymer and a wax to form an admixture; and c) cooling the admixture to a temperature at or less than the solidification temperature of the thermoplastic polymer in 10 seconds or less. The mixing can be at a shear rate of greater than $10 \text{ s}^{-1}$, or about 30 to about 100 $\text{s}^{-1}$. The admixture can be cooled in 10 seconds or less to a temperature of 50° C. or less. The composition can be pelletized. The pelletizing can occur after cooling the admixture or before or simultaneous to cooling the admixture. The composition can be made using an extruder, such as a single- or twin-screw extruder. Alternatively, the method of making a composition can comprise a) melting a thermoplastic polymer to form a molten thermoplastic polymer; b) mixing the molten thermoplastic polymer and a wax to form an admixture; and c) spinning the molten mixture to form filaments or fibers which solidify upon cooling.

BRIEF DESCRIPTION OF THE DRAWINGS

For a more complete understanding of the disclosure, reference should be made to the following detailed description and accompanying drawing wherein:

FIGS. 4-6 show Table 1.

FIGS. 7 and 8 show Table 2.

FIGS. 9 and 10 show Table 3.

Figure 1:
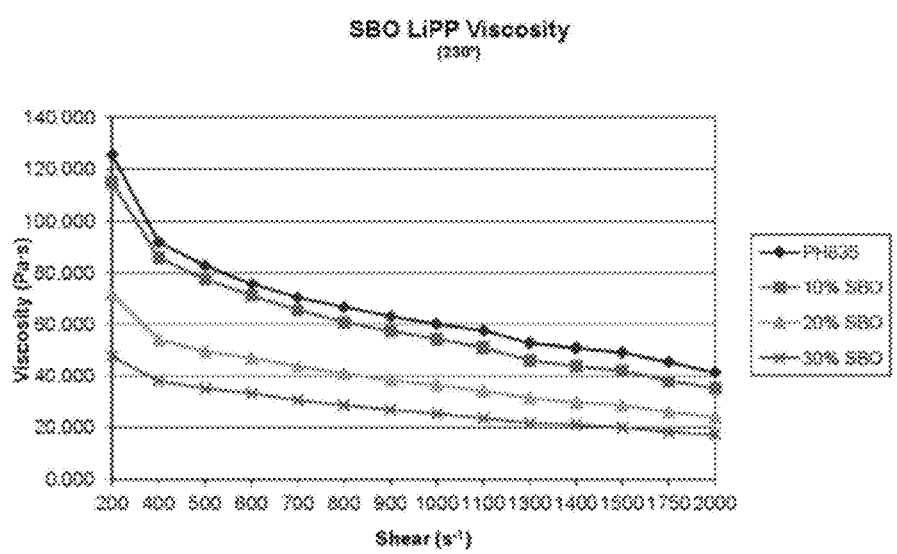
FIG. 1 shows the viscosity of unmodified polypropylene and Examples 1-3, compositions as disclosed herein.

While the disclosed invention is susceptible of embodiments in various forms, there are illustrated in the drawings (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

Fibers disclosed herein are made by melt spinning compositions of an intimate admixture of a thermoplastic polymer and a wax. The term "intimate admixture" refers to the physical relationship of the wax and thermoplastic polymer, wherein the wax is dispersed within the thermoplastic polymer. The droplet size of the wax within the thermoplastic polymer is a parameter that indicates the level of dispersion of the wax within the thermoplastic polymer. The smaller the droplet size, the higher the dispersion of the wax within the thermoplastic polymer, the larger the droplet size the lower the dispersion of the wax within the thermoplastic polymer. As used herein, the term "admixture" refers to the intimate admixture of the one of the inventions disclosed herein, and not an "admixture" in the more general sense of a standard mixture of materials.

The droplet size of the wax within the thermoplastic polymer is less than 2 µm and can be less than 1 µm, or less than 500 nm. Other contemplated droplet sizes of the wax dispersed within the thermoplastic polymer include less than 1.5 µm, less than 900 nm, less than 800 nm, less than 700 nm, less than 600 nm, less than 400 nm, less than 300 nm, and less than 200 nm.

The droplet size of the wax can be measured by scanning electron microscopy (SEM) indirectly by measuring a void size in the thermoplastic polymer, after removal of the wax from the composition. Removal of the wax is typically performed prior to SEM imaging due to incompatibility of the wax and the SEM imaging technique. Thus, the void measured by SEM imaging is correlated to the droplet size of the wax in the composition, as exemplified in FIG. 2.

One exemplary way to achieve a suitable dispersion of the wax within the thermoplastic polymer is by admixing the thermoplastic polymer, in a molten state, and the wax. The thermoplastic polymer is melted (e.g., exposed to temperatures greater than the thermoplastic polymer's solidification temperature) to provide the molten thermoplastic polymer and mixed with the wax. The thermoplastic polymer can be melted prior to addition of the wax or can be melted in the presence of the wax. It should be understood that when the polymer is melted, the wax is also in the molten state. The term wax hereafter can refer to the component either in the solid (optionally crystalline) state or in the molten state, depending on the temperature. It is not required that the wax be solidified at a temperature at which the polymer is solidified. For example, polypropylene is a semi-crystalline solid at 90° C., which is above the melting point of many waxes.

The thermoplastic polymer and wax can be mixed, for example, at a shear rate of greater than $10 s^{-1}$. Other contemplated shear rates include greater than 10, about 15 to about 1000, about 20 to about 200 or up to 500 $s^{-1}$. The higher the shear rate of the mixing, the greater the dispersion of the wax in the composition as disclosed herein. Thus, the dispersion can be controlled by selecting a particular shear rate during formation of the composition.

The wax and molten thermoplastic polymer can be mixed using any mechanical means capable of providing the necessary shear rate to result in a composition as disclosed herein. Non-limiting examples of mechanical means include a mixer, such as a Haake batch mixer, and an extruder (e.g., a single- or twin-screw extruder).

The mixture of molten thermoplastic polymer and wax is then rapidly (e.g., in less than 10 seconds) cooled to a temperature lower than the solidification temperature (either via traditional thermoplastic polymer crystallization or passing below the polymer glass transition temperature) of the thermoplastic polymer. The admixture can be cooled to less than 200° C., less than 150° C., less than 100° C. less than 75° C., less than 50° C., less than 40° C., less than 30° C., less than 20° C., less than 15° C., less than 10° C., or to a temperature of about 0° C. to about 30° C., about 0° C. to about 20° C., or about 0° C. to about 10° C. For example, the mixture can be placed in a low temperature liquid (e.g., the liquid is at or below the temperature to which the mixture is cooled) or gas. The liquid can be ambient or controlled temperature water. The gas can be ambient air or controlled temperature and humidity air. Any quenching media can be used so long as it cools the admixture rapidly. Additional liquids such as oils, alcohols and ketones can be used for quenching, along with mixtures comprising water (sodium chloride for example) depending on the admixture composition. Additional gases can be used, such as carbon dioxide and nitrogen, or any other component naturally occurring in atmospheric temperature and pressure air.

Optionally, the composition is in the form of pellets. Pellets of the composition can be formed prior to, simultaneous to, or after cooling of the mixture. The pellets can be formed by strand cutting or underwater pelletizing. In strand cutting, the composition is rapidly quenched (generally in a time period much less than 10 seconds) then cut into small pieces. In underwater pelletizing, the mixture is cut into small pieces and simultaneously or immediately thereafter placed in the presence of a low temperature liquid that rapidly cools and solidifies the mixture to form the pelletized composition. Such pelletizing methods are well understood by the ordinarily skilled artisan. Pellet morphologies can be round or cylindrical, and can have no dimension larger than 15 mm, more preferably less than 10 mm, or no dimension larger than 5 mm.

Alternatively, the admixture (admixture and mixture or used interchangeably here within this document) can be used whilst mixed in the molten state and formed directly into fibers.

Thermoplastic Polymers

Thermoplastic polymers, as used in the disclosed compositions, are polymers that melt and then, upon cooling, crystallize or harden, but can be re-melted upon further heating. Suitable thermoplastic polymers used herein have a melting temperature from about 60° C. to about 300° C., from about 80° C. to about 250° C., or from 100° C. to 215° C.

The thermoplastic polymers can be derived from renewable resources or from fossil minerals and oils. The thermoplastic polymers derived from renewable resources are bio-based, for example such as bio produced ethylene and propylene monomers used in the production polypropylene and polyethylene. These material properties are essentially identical to fossil based product equivalents, except for the presence of carbon-14 in the thermoplastic polymer. Renewable and fossil based thermoplastic polymers can be combined together in any of the embodiments of the invention disclosed herein in any ratio, depending on cost and availability. Recycled thermoplastic polymers can also be used, alone or in combination with renewable and/or fossil derived thermoplastic polymers. The recycled thermoplastic polymers can be pre-conditioned to remove any unwanted contaminants prior to compounding or they can be used during the compounding and extrusion process, as well as simply left in the admixture. These contaminants can include trace amounts of other polymers, pulp, pigments, inorganic compounds, organic compounds and other additives typically found in processed polymeric compositions. The contaminants should not negatively impact the final performance properties of the admixture, for example, causing spinning breaks during a fiber spinning process.

The molecular weight of the thermoplastic polymer is sufficiently high to enable entanglement between polymer molecules and yet low enough to be melt spinnable. Addition of the wax into the composition allows for compositions containing higher molecular weight thermoplastic polymers to be spun, compared to compositions without a wax. Thus, suitable thermoplastic polymers can have weight average molecular weights of about 1000 kDa or less, about 5 kDa to about 800 kDa, about 10 kDa to about 700 kDa, or about 20 kDa to about 400 kDa. The weight average molecular weight is determined by the specific method for each polymer, but is generally measured using either gel permeation chromatography (GPC) or from solution viscosity measurements. The thermoplastic polymer weight average molecular weight should be determined before addition into the admixture.

Suitable thermoplastic polymers generally include polyolefins, polyesters, polyamides, copolymers thereof, and combinations thereof. The thermoplastic polymer can be selected from the group consisting of polypropylene, polyethylene, polypropylene co-polymer, polyethylene co-polymer, polyethylene terephthalate, polybutylene terephthalate, polylactic acid, polyhydroxyalkanoates, polyamide-6, polyamide-6,6, and combinations thereof.

More specifically, however, the thermoplastic polymers preferably include polyolefins such as polyethylene or copolymers thereof, including low density, high density, linear low density, or ultra low density polyethylenes such that the polyethylene density ranges between 0.90 grams per cubic centimeter to 0.97 grams per cubic centimeter, most preferred between 0.92 and 0.95 grams per cubic centimeter. The density of the polyethylene will is determined by the amount and type of branching and depends on the polymerization technology and comonomer type. Polypropylene and/or polypropylene copolymers, including atactic polypropylene; isotactic polypropylene, syndiotactic polypropylene, and combination thereof can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin.

Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; polyacrylates, polymethacrylates, and their copolymers such as poly(methyl methacrylates). Other nonlimiting examples of polymers include polycarbonates, polyvinyl acetates, poly(oxymethylene), styrene copolymers, polyacrylates, polymethacrylates, poly(methyl methacrylates), polystyrene/methyl methacrylate copolymers, polyetherimides, polysulfones, or combinations thereof. In some embodiments, thermoplastic polymers include polypropylene, polyethylene, polyamides, polyvinyl alcohol, ethylene acrylic acid, polyolefin carboxylic acid copolymers, polyesters, and combinations thereof.

Biodegradable thermoplastic polymers also are contemplated for use herein. Biodegradable materials are susceptible to being assimilated by microorganisms, such as molds, fungi, and bacteria when the biodegradable material is buried in the ground or otherwise contacts the microorganisms (including contact under environmental conditions conducive to the growth of the microorganisms). Suitable biodegradable polymers also include those biodegradable materials which are environmentally-degradable using aerobic or anaerobic digestion procedures, or by virtue of being exposed to environmental elements such as sunlight, rain, moisture, wind, temperature, and the like. The biodegradable thermoplastic polymers can be used individually or as a combination of biodegradable or non-biodegradable polymers. Biodegradable polymers include polyesters containing aliphatic components. Among the polyesters are ester polycondensates containing aliphatic constituents and poly(hydroxycarboxylic) acid. The ester polycondensates include diacids/diol aliphatic polyesters such as polybutylene succinate, polybutylene succinate co-adipate, aliphatic/aromatic polyesters such as terpolymers made of butylene diol, adipic acid and terephthalic acid. The poly(hydroxycarboxylic) acids include lactic acid based homopolymers and copolymers, polyhydroxybutyrate (PHB), or other polyhydroxyalkanoate homopolymers and copolymers. Such polyhydroxyalkanoates include copolymers of PHB with higher chain length monomers, such as $C_6$-$C_{12}$, and higher, polyhydroxyalkanaotes, such as those disclosed in U.S. Pat. Nos. Re. 36,548 and 5,990,271.

An example of a suitable commercially available polylactic acid is NATUREWORKS from Cargill Dow and LACEA from Mitsui Chemical. An example of a suitable commercially available diacid/diol aliphatic polyester is the polybutylene succinate/adipate copolymers sold as BIONOLLE 1000 and BIONOLLE 3000 from the Showa High Polymer Company, Ltd. (Tokyo, Japan). An example of a suitable commercially available aliphatic/aromatic copolyester is the poly(tetramethylene adipate-co-terephthalate) sold as EASTAR BIO Copolyester from Eastman Chemical or ECOFLEX from BASF.

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), and Mosten NB425 (a 25 melt flow rate Ziegler-Natta isotactic polypropylene from Unipetrol). Other suitable polymer may include Danimer 27510 (a polyhydroxyalkanoate polypropylene from Danimer Scientific LLC), Dow Aspun 6811A (a 27 melt index polyethylene octene copolymer from Dow Chemical), and Eastman 9921 (a polyester terephthalic homopolymer with a nominally 0.81 intrinsic viscosity from Eastman Chemical).

The thermoplastic polymer component can be a single polymer species as described above or a blend of two or more thermoplastic polymers as described above.

If the polymer is polypropylene, the thermoplastic polymer can have a melt flow index of greater than 0.5 g/10 min, as measured by ASTM D-1238, used for measuring polypropylene. Other contemplated melt flow indices include greater than 5 g/10 min, greater than 10 g/10 min, or about 5 g/10 min to about 50 g/10 min.

Waxes

A wax, as used in the disclosed composition, is a lipid, mineral wax, or combination thereof, wherein the lipid, mineral wax, or combination thereof has a melting point of greater than 25° C. More preferred is a melting point above 35° C., still more preferred above 45° C. and most preferred above 50° C. The wax can have a melting point that is lower than the melting temperature of the thermoplastic polymer in the composition. The terms "wax" and "oil" are differentiated by crystallinity of the component at or near 25° C. In all cases, the "wax" will have a maximum melting temperature less than the thermoplastic polymer, preferably less than 100° C. and most preferably less than 80° C. The wax can be a lipid. The lipid can be a monoglyceride, diglyceride, triglyceride, fatty acid, fatty alcohol, esterified fatty acid, epoxidized lipid, maleated lipid, hydrogenated lipid, alkyd resin derived from a lipid, sucrose polyester, or combinations thereof. The mineral wax can be a linear alkane, a branched alkane, or combinations thereof. The waxes can be partially or fully hydrogenated materials, or combinations and mixtures thereof, that were formally liquids at room temperature in their unmodified forms. When the temperature is above the melting temperature of the wax, it is a liquid oil. When in the molten state, the wax can be referred to as an "oil". The terms "wax" and "oil" only have meaning when measured at 25° C. The wax will be a solid at 25° C., while an oil is not a solid at 25° C. Otherwise they are used interchangeably above 25° C.

Because the wax may contain a distribution of melting temperatures to generate a peak melting temperature, the wax melting temperature is defined as having a peak melting temperature 25° C. or above as defined as when >50 weight percent of the wax component melts at or above 25° C. This measurement can be made using a differential scanning calorimeter (DSC), where the heat of fusion is equated to the weight percent fraction of the wax.

The wax number average molecular weight, as determined by gel permeation chromatography (GPC), should be less than 2 kDa, preferably less than 1.5 kDa, still more preferred less than 1.2 kDa.

The amount of wax is determined via gravimetric weight loss method. The solidified mixture is placed, with the narrowest specimen dimension no greater than 1 mm, into acetone at a ratio of 1 g or mixture per 100 g of acetone using a refluxing flask system. First the mixture is weighed before being placed into the reflux flask, and then the acetone and mixtures are heated to 60° C. for 20 hours. The sample is removed and air dried for 60 minutes and a final weight determined. The equation for calculating the weight percent wax is $$\text{weight \% wax} = ([\text{initial mass-final mass}]/[\text{initial mass}]) \times 100\%$$

Non-limiting examples of waxes contemplated in the compositions disclosed herein include beef tallow, castor wax, coconut wax, coconut seed wax, corn germ wax, cottonseed wax, fish wax, linseed wax, olive wax, oiticica wax, palm kernel wax, palm wax, palm seed wax, peanut wax, rapeseed wax, safflower wax, soybean wax, sperm wax, sunflower seed wax, tall wax, tung wax, whale wax, and combinations thereof. Non-limiting examples of specific triglycerides include triglycerides such as, for example, tristearin, tripalmitin, 1,2-dipalmitoolein, 1,3-dipalmitoolein, 1-palmito-3-stearo-2-olein, 1-palmito-2-stearo-3-olein, 2-palmito-1-stearo-3-olein, 1,2-dipalmitolinolein, 1,2-distearo-olein, 1,3-distearo-olein, trimyristin, trilaurin and combinations thereof. Non-limiting examples of specific fatty acids contemplated include capric acid, caproic acid, caprylic acid, lauric acid, myristic acid, palmitic acid, stearic acid, and mixtures thereof. Other specific waxes contemplated include hydrogenated soy bean oil, partially hydrogenated soy bean oil, partially hydrogenated palm kernel oil, and combinations thereof. Inedible waxes from Jatropha and rapeseed oil can also be used. The wax can be selected from the group consisting of a hydrogenated plant oil, a partially hydrogenated plant oil, an epoxidized plant oil, a maleated plant oil. Specific examples of such plant oils include soy bean oil, corn oil, canola oil, and palm kernel oil. Specific examples of mineral wax include paraffin (including petrolatum), Montan wax, as well as polyolefin waxes produced from cracking processes, preferentially polyethylene derived waxes. Mineral waxes and plant derived waxes can be combined together. Plant based waxes can be differentiated by their carbon-14 content.

The wax can be from a renewable material (e.g., derived from a renewable resource). As used herein, a "renewable resource" is one that is produced by a natural process at a rate comparable to its rate of consumption (e.g., within a 100 year time frame). The resource can be replenished naturally, or via agricultural techniques. Non-limiting examples of renewable resources include plants (e.g., sugar cane, beets, corn, potatoes, citrus fruit, woody plants, lignocellulosics, hemicellulosics, cellulosic waste), animals, fish, bacteria, fungi, and forestry products. These resources can be naturally occurring, hybrids, or genetically engineered organisms. Natural resources such as crude oil, coal, natural gas, and peat, which take longer than 100 years to form, are not considered renewable resources.

The wax, as disclosed herein, can be present in the composition at a weight percent of 1 wt % to 20 wt %, based upon the total weight of the composition. Other contemplated wt % ranges of the wax include 2 wt % to 15 wt %, with a preferred range from about 3 wt % to about 10 wt %. Specific wax wt % contemplated include about 1 wt %, 2 wt %, 3 wt %, 4 wt %, 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, and about 20 wt, based upon the total weight of the composition.

Additives

The compositions disclosed herein can further include an additive. The additive can be dispersed throughout the composition, or can be substantially in the thermoplastic polymer portion of the thermoplastic layer or substantially in the wax portion of the composition. In cases where the additive is in the wax portion of the composition, the additive can be wax soluble or wax dispersible.

Non-limiting examples of classes of additives contemplated in the compositions disclosed herein include perfumes, dyes, pigments, nanoparticles, antistatic agents, fillers, and combinations thereof. The compositions disclosed herein can contain a single additive or a mixture of additives. For example, both a perfume and a colorant (e.g., pigment and/or dye) can be present in the composition. The additive(s), when present, is/are present in a weight percent of 0.05 wt % to 20 wt %, or 0.1 wt % to 10 wt %. Specifically contemplated weight percentages include 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, 5 wt %, 5.1 wt %, 5.2 wt %, 5.3 wt %, 5.4 wt %, 5.5 wt %, 5.6 wt %, 5.7 wt %, 5.8 wt %, 5.9 wt %, 6 wt %, 6.1 wt %, 6.2 wt %, 6.3 wt %, 6.4 wt %, 6.5 wt %, 6.6 wt %, 6.7 wt %, 6.8 wt %, 6.9 wt %, 7 wt %, 7.1 wt %, 7.2 wt %, 7.3 wt %, 7.4 wt %, 7.5 wt %, 7.6 wt %, 7.7 wt %, 7.8 wt %, 7.9 wt %, 8 wt %, 8.1 wt %, 8.2 wt %, 8.3 wt %, 8.4 wt %, 8.5 wt %, 8.6 wt %, 8.7 wt %, 8.8 wt %, 8.9 wt %, 9 wt %, 9.1 wt %, 9.2 wt %, 9.3 wt %, 9.4 wt %, 9.5 wt %, 9.6 wt %, 9.7 wt %, 9.8 wt %, 9.9 wt %, and 10 wt %.

As used herein the term "perfume" is used to indicate any odoriferous material that is subsequently released from the composition as disclosed herein. A wide variety of chemicals are known for perfume uses, including materials such as aldehydes, ketones, alcohols, and esters. More commonly, naturally occurring plant and animal oils and exudates including complex mixtures of various chemical components are known for use as perfumes. The perfumes herein can be relatively simple in their compositions or can include highly sophisticated complex mixtures of natural and synthetic chemical components, all chosen to provide any desired odor. Typical perfumes can include, for example, woody/earthy bases containing exotic materials, such as sandalwood, civet and patchouli oil. The perfumes can be of a light floral fragrance (e.g. rose extract, violet extract, and lilac). The perfumes can also be formulated to provide desirable fruity odors, e.g. lime, lemon, and orange. The perfumes delivered in the compositions and articles disclosed herein can be selected for an aromatherapy effect, such as providing a relaxing or invigorating mood. As such, any material that exudes a pleasant or otherwise desirable odor can be used as a perfume active in the compositions and articles disclosed herein.

A pigment or dye can be inorganic, organic, or a combination thereof. Specific examples of pigments and dyes contemplated include pigment Yellow (C.I. 14), pigment Red (C.I. 48:3), pigment Blue (C.I. 15:4), pigment Black (C.I. 7), and combinations thereof. Specific contemplated dyes include water soluble ink colorants like direct dyes, acid dyes, base dyes, and various solvent soluble dyes. Examples include, but are not limited to, FD&C Blue 1 (C.I. 42090:2), D&C Red 6(C.I. 15850), D&C Red 7(C.I. 15850:1), D&C Red 9(C.I. 15585:1), D&C Red 21(C.I. 45380:2), D&C Red 22(C.I. 45380:3), D&C Red 27(C.I. 45410:1), D&C Red 28(C.I. 45410:2), D&C Red 30(C.I. 73360), D&C Red 33(C.I. 17200), D&C Red 34(C.I. 15880:1), and FD&C Yellow 5(C.I. 19140:1), FD&C Yellow 6(C.I. 15985:1), FD&C Yellow 10(C.I. 47005:1), D&C Orange 5(C.I. 45370:2), and combinations thereof.

Contemplated fillers include, but are not limited to inorganic fillers such as, for example, the oxides of magnesium, aluminum, silicon, and titanium. These materials can be added as inexpensive fillers or processing aides. Other inorganic materials that can function as fillers include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, can be used. Additionally, alkyd resins can also be added to the composition. Alkyd resins comprise a polyol, a polyacid or anhydride, and/or a fatty acid.

Additional contemplated additives include nucleating and clarifying agents for the thermoplastic polymer. Specific examples, suitable for polypropylene, for example, are benzoic acid and derivatives (e.g. sodium benzoate and lithium benzoate), as well as kaolin, talc and zinc glycerolate. Dibenzlidene sorbitol (DBS) is an example of a clarifying agent that can be used. Other nucleating agents that can be used are organocarboxylic acid salts, sodium phosphate and metal salts (for example aluminum dibenzoate) The nucleating or clarifying agents can be added in ranges from 20 parts per million (20ppm) to 20,000 ppm, more preferred range of 200 ppm to 2000 ppm and the most preferred range from 1000 ppm to 1500 ppm. The addition of the nucleating agent can be used to improve the tensile and impact properties of the finished admixture composition.

Contemplated surfactants include anionic surfactants, amphoteric surfactants, or a combination of anionic and amphoteric surfactants, and combinations thereof, such as surfactants disclosed, for example, in U.S. Pat. Nos. 3,929,678 and 4,259,217 and in EP 414 549, WO93/08876 and WO93/08874.

Contemplated nanoparticles include metals, metal oxides, allotropes of carbon, clays, organically modified clays, sulfates, nitrides, hydroxides, oxy/hydroxides, particulate water-insoluble polymers, silicates, phosphates and carbonates. Examples include silicon dioxide, carbon black, graphite, grapheme, fullerenes, expanded graphite, carbon nanotubes, talc, calcium carbonate, betonite, montmorillonite, kaolin, zinc glycerolate, silica, aluminosilicates, boron nitride, aluminum nitride, barium sulfate, calcium sulfate, antimony oxide, feldspar, mica, nickel, copper, iron, cobalt, steel, gold, silver, platinum, aluminum, wollastonite, aluminum oxide, zirconium oxide, titanium dioxide, cerium oxide, zinc oxide, magnesium oxide, tin oxide, iron oxides ($Fe_2O_3$, $Fe_3O_4$) and mixtures thereof. Nanoparticles can increase strength, thermal stability, and/or abrasion resistance of the compositions disclosed herein, and can give the compositions electric properties.

It is contemplated to add oils or that some amount of oil is present in the composition. The oil may be unrelated to the lipid present or can be an unsaturated or less saturated version of the wax lipid. The amount of oil present can range from 0 weight percent to 40 weight percent of the composition, more preferably from 5 weight percent to 20 weight percent of the composition and most preferably from 8 weight percent to 15 weight percent of the composition.

Contemplated anti-static agents include fabric softeners which are known to provide antistatic benefits. For example those fabric softeners that have a fatty acyl group which has an iodine value of above 20, such as N,N-di(tallowoyl-oxy-ethyl)-N,N-dimethyl ammonium methylsulfate.

Fibers

In one embodiment, the fibers may be monocomponent or multicomponent. The term "fiber" is defined as a solidified polymer shape with a length to thickness ratio of greater than 1,000. The monocomponent fibers may also be multiconstituent. Constituent, as used herein, is defined as meaning the chemical species of matter or the material. Multiconstituent fiber, as used herein, is defined to mean a fiber containing more than one chemical species or material. Multiconstituent and alloyed polymers have the same meaning herein and can be used interchangeably. Generally, fibers may be of monocomponent or multicomponent types. Component, as used herein, is defined as a separate part of the fiber that has a spatial relationship to another part of the fiber. The term multicomponent, as used herein, is defined as a fiber having more than one separate part in spatial relationship to one another. The term multicomponent includes bicomponent, which is defined as a fiber having two separate parts in a spatial relationship to one another. The different components of multicomponent fibers are arranged in substantially distinct regions across the cross-section of the fiber and extend continuously along the length of the fiber. Methods for making multicomponent fibers are well known in the art. Multicomponent fiber extrusion was well known in the 1960's. DuPont was a lead technology developer of multicomponent capability, with U.S. Pat. No. 3,244,785 and U.S. Pat. No. 3,704,971 providing a technology description of the technology used to make these fibers. "Bicomponent Fibers" by R. Jeffries from Merrow Publishing in 1971 laid a solid groundwork for bicomponent technology. More recent publications include "Taylor-Made Polypropylene and Bicomponent Fibers for the Nonwoven Industry," Tappi Journal December 1991 (p103) and "Advanced Fiber Spinning Technology" edited by Nakajima from Woodhead Publishing.

The nonwoven fabric disclosed herein may contain multiple types of monocomponent fibers that are delivered from different extrusion systems through the same spinneret. The extrusion system, in this example, is a multicomponent extrusion system that delivers different polymers to separate capillaries. For instance, one extrusion system would deliver polypropylene with wax and the other a polypropylene copolymer such that the copolymer composition melts at different temperatures. In a second example, one extrusion system might deliver a polyethylene resin and the other polypropylene with wax. In a third example, one extrusion system might deliver a polypropylene resin with 30 weight percent wax and the other a polypropylene resin with 30 weight percent wax that has a molecular weight different from the first polypropylene resin. The polymer ratios in this system can range from 95:5 to 5:95, preferably from 90:10 to 10:90 and 80:20 to 20:80.

Bicomponent and multicomponent fibers may be in a side-by-side, sheath-core (symmetric and eccentric), segmented pie, ribbon, islands-in-the-sea configuration, or any combination thereof. The sheath may be continuous or non-continuous around the core. Non-inclusive examples of exemplarily multicomponent fibers are disclosed in U.S. Pat. No. 6,746,766. The ratio of the weight of the sheath to the core is from about 5:95 to about 95:5. The fibers disclosed herein may have different geometries that include, but are not limited to; round, elliptical, star shaped, trilobal, multi-lobal with 3-8 lobes, rectangular, H-shaped, C-shaped, I-shape, U-shaped and other various eccentricities. Hollow fibers can also be used. Preferred shapes are round, trilobal and H-shaped. The round and trilobal fiber shapes can also be hollow.

Sheath and core bicomponent fibers are preferred. In one preferred case, the component in the core may contain the thermoplastic polymer and wax, while the sheath does not. In this case the exposure to wax at the surface of the fiber is reduced or eliminated. In another preferred case, the sheath may contain the wax and the core does not. In this case the concentration of wax at the fiber surface is higher than in the core. Using sheath and core bicomponent fibers, the concentration of the wax can be selected to impart desired properties either in the sheath or core, or some concentration gradient. It should be understood that islands-in-a-sea bicomponent fibers are considered to be a type of sheath and core fiber, but with multiple cores. Segmented pie fibers (hollow and solid) are contemplated. For one example, to split regions that contain wax from regions that do not contain wax using segmented pie type of bicomponent fiber design. Splitting may occur during mechanical deformation, application of hydrodynamic forces or other suitable processes.

Tricomponent fibers are also contemplated. One example of a useful tricomponent fiber would be a three layered sheath/sheath/core fiber, where each component contains a different amount of wax. Different amounts of wax in each layer may provide additional benefits. For example, the core can be a blend of 10 melt flow polypropylene with 30 weight percent wax. The middle layer sheath may be a blend of 25 melt flow polypropylene with 20 weight percent wax and the outer layer may be straight 35 melt flow rate polypropylene. It is preferred that the wax content between each layer is less than 40 wt %, more preferably less than 20 wt %. Another type of useful tricomponent fiber contemplated is a segmented pie type bicomponent design that also has a sheath.

A "highly attenuated fiber" is defined as a fiber having a high draw down ratio. The total fiber draw down ratio is defined as the ratio of the fiber at its maximum diameter (which is typically results immediately after exiting the capillary) to the final fiber diameter in its end use. The total fiber draw down ratio will be greater than 1.5, preferable greater than 5, more preferably greater than 10, and most preferably greater than 12. This is necessary to achieve the tactile properties and useful mechanical properties.

The fiber will have a diameter of less than 50 μm. The diameter of the fibers made with any of the previously discussed compositions can be as low as 0.1 μm if the mixture is being used to produce fine fibers. The fibers can be either essentially continuous or essentially discontinuous. Fibers commonly used to make spunbond nonwovens that are made with any of the previously discussed compositions will have a diameter of from 5 μm to 30 μm, more preferably from 10 μm to 20 μm and most preferred from 12 μm to about 18 μm. Fine fiber diameter will have a diameter from 0.1 μm to 5 μm, preferably from 0.2 μm to 3 μm and most preferred from 0.3 μm to 2 μm Fiber diameter is controlled by die geometry, spinning speed or drawing speed, mass through-put, and blend composition and rheology. The fibers as described herein can be environmentally degradable.

The fibers described herein are typically used to make disposable articles that include at least one layer of fibers made with any of the compositions previously discussed, and which can be in the form of a nonwoven material. The articles can be flushable. The term "flushable" as used herein refers to materials which are capable of dissolving, dispersing, disintegrating, and/or decomposing in a septic disposal system such as a toilet to provide clearance when flushed down the toilet without clogging the toilet or any other sewage drainage pipe. The fibers and resulting articles may also be aqueous responsive. The term aqueous responsive as used herein means that when placed in water or flushed, an observable and measurable change will result. Typical observations include noting that the article swells, pulls apart, dissolves, or observing a general weakened structure.

The hydrophilicity and hydrophobicity of the fibers can be adjusted as needed. The base resin properties can have hydrophilic properties via copolymerization (such as the case for certain polyesters (EASTONE from Eastman Chemical, the sulfopolyester family of polymers in general) or polyolefins such as polypropylene or polyethylene) or have materials added to the base resin to render it hydrophilic. Exemplarily examples of additives include CIBA Irgasurf® family of additives. The fibers in the present invention can also be treated or coated after they are made to render them hydrophilic. In the present invention, durable hydrophilicity is preferred. Durable hydrophilicity is defined as maintaining hydrophilic characteristics after more than one fluid interaction. For example, if the sample being evaluated is tested for durable hydrophilicity, water can be poured on the sample and wetting observed. If the sample wets out it is initially hydrophilic. The sample is then completely rinsed with water and dried. The rinsing is best done by putting the sample in a large container and agitating for ten seconds and then drying. The sample after drying should also wet out when contacted again with water.

After the fiber is formed, the fiber may further be treated or the bonded fabric can be treated. A hydrophilic or hydrophobic finish can be added to adjust the surface energy and chemical nature of the fabric. For example, fibers that are hydrophobic may be treated with wetting agents to facilitate absorption of aqueous liquids. A bonded fabric can also be treated with a topical solution containing surfactants, pigments, slip agents, salt, or other materials to further adjust the surface properties of the fiber.

In one embodiment, the fibers can be crimped, although it can be preferred that they are not crimped. Crimped fibers are generally produced in two methods. The first method is mechanical deformation of the fiber after it is already spun. Fibers are melt spun, drawn down to the final filament diameter and mechanically treated, generally through gears or a stuffer box that imparts either a two dimensional or three dimensional crimp. This method is used in producing most carded staple fibers. The second method for crimping fibers is to extrude multicomponent fibers that are capable of crimping in a spunlaid process. One of ordinary skill in the art would recognize that a number of methods of making bicomponent crimped spunbond fibers exists; however, three main techniques are considered for making crimped spunlaid nonwovens. The first is crimping that occurs in the spinline due to differential polymer crystallization in the spinline, a result of differences in polymer type, polymer molecular weight characteristics (e.g., molecular weight distribution) or additives content. A second method is differential shrinkage of the fibers after they have been spun into a spunlaid substrate. For instance, heating the spunlaid web can cause fibers to shrink due to differences in crystallinity in the as-spun fibers, for example during the thermal bonding process. A third method of causing crimping is to mechanically stretch the fibers or spunlaid web (generally for mechanical stretching the web has been bonded together). The mechanical stretching can expose differences in the stress-strain curve between the two polymer components, which can cause crimping.

The tensile strength of a fiber is approximately greater than 25 Mega Pascal (MPa). The fibers as disclosed herein have a tensile strength of greater than about 50 MPa, preferably greater than about 75 MPa, and more preferably greater than about 100 MPa. Tensile strength is measured using an Instron following a procedure described by ASTM standard D 3822-91 or an equivalent test.

The fibers as disclosed herein are not brittle and have a toughness of greater than 2 MPa, greater than 50 MPa, or greater than 100 MPa. Toughness is defined as the area under the stress-strain curve where the specimen gauge length is 25 mm with a strain rate of 50 mm per minute. Elasticity or extensibility of the fibers may also be desired.

The fibers as disclosed herein can be thermally bondable if sufficient thermoplastic polymers are present in the fiber or on the outside component of the fiber (i.e. sheath of a bicomponent). Thermally bondable fibers are best used in the pressurized heat and thru-air heat bonding methods. Thermally bondable is typically achieved when the composition is present at a level of greater than about 15%, preferably greater than about 30%, most preferably greater than about 40%, and most preferably greater than about 50% by weight of the fiber.

The fibers disclosed herein can be environmentally degradable depending upon the amount of the composition that is present and the specific configuration of the fiber. "Environmentally degradable" is defined as being biodegradable, disintigratable, dispersible, flushable, or compostable or a combination thereof. The fibers, nonwoven webs, and articles can be environmentally degradable. As a result, the fibers may be easily and safely disposed of either in existing composting facilities or may be flushable and can be safely flushed down the drain without detrimental consequences to existing sewage infrastructure systems. The flushability of the fibers when used in disposable products such as wipes and feminine hygiene items offer additional convenience and discretion to the consumer.

The term "biodegradable" refers to matter that, when exposed to an aerobic and/or anaerobic environment, is eventually reduced to monomeric components due to microbial, hydrolytic, and/or chemical actions. Under aerobic conditions, biodegradation leads to the transformation of the material into end products such as carbon dioxide and water. Under anaerobic conditions, biodegradation leads to the transformation of the materials into carbon dioxide, water, and methane. The biodegradability process is often described as mineralization. Biodegradability means that all organic constituents of the matter (e.g., fibers) are subject to decomposition eventually through biological activity.

There are a variety of different standardized biodegradability methods that have been established over time by various organizations and in different countries. Although the tests vary in the specific testing conditions, assessment methods, and criteria desired, there is reasonable convergence between different protocols so that they are likely to lead to similar conclusions for most materials. For aerobic biodegradability, the American Society for Testing and Materials (ASTM) has established ASTM D 5338-92: Test methods for Determining Aerobic Biodegradation of Plastic Materials under Controlled Composting Conditions. The ASTM test measures the percent of test material that mineralizes as a function of time by monitoring the amount of carbon dioxide being released as a result of assimilation by microorganisms in the presence of active compost held at a thermophilic temperature of 58° C. Carbon dioxide production testing may be conducted via electrolytic respirometry. Other standard protocols, such 301B from the Organization for Economic Cooperation and Development (OECD), may also be used. Standard biodegradation tests in the absence of oxygen are described in various protocols such as ASTM D 5511-94. These tests are used to simulate the biodegradability of materials in an anaerobic solid-waste treatment facility or sanitary landfill. However, these conditions are less relevant for the type of disposable applications that are described for the fibers and nonwovens as described herein.

Disintegration occurs when the fibrous substrate has the ability to rapidly fragment and break down into fractions small enough not to be distinguishable after screening when composted or to cause drainpipe clogging when flushed. A disintegratable material will also be flushable. Most protocols for disintegradability measure the weight loss of test materials over time when exposed to various matrices. Both aerobic and anaerobic disintegration tests are used. Weight loss is determined by the amount of fibrous test material that is no longer collected on an 18 mesh sieve with 1 millimeter openings after the materials is exposed to wastewater and sludge. For disintegration, the difference in the weight of the initial sample and the dried weight of the sample recovered on a screen will determine the rate and extent of disintegration. The testing for biodegradability and disintegration are very similar as a very similar environment, or the same environment, will be used for testing. To determine disintegration, the weight of the material remaining is measured while for biodegradability, the evolved gases are measured. The fibers disclosed herein can rapidly disintegrate.

The fibers as disclosed herein can also be compostable. ASTM has developed test methods and specifications for compostability. The test measures three characteristics: biodegradability, disintegration, and lack of ecotoxicity. Tests to measure biodegradability and disintegration are described above. To meet the biodegradability criteria for compostability, the material must achieve at least about 60% conversion to carbon dioxide within 40 days. For the disintegration criteria, the material must have less than 10% of the test material remain on a 2 millimeter screen in the actual shape and thickness that it would have in the disposed product. To determine the last criteria, lack of ecotoxicity, the biodegradation byproducts must not exhibit a negative impact on seed germination and plant growth. One test for this criteria is detailed in OECD 208. The International Biodegradable Products Institute will issue a logo for compostability once a product is verified to meet ASTM 6400-99 specifications. The protocol follows Germany's DIN 54900 which determine the maximum thickness of any material that allows complete decomposition within one composting cycle.

The fibers described herein can be used to make disposable nonwoven articles. The articles are commonly flushable. The term "flushable" as used herein refers to materials which are capable of dissolving, dispersing, disintegrating, and/or decomposing in a septic disposal system such as a toilet to provide clearance when flushed down the toilet without clogging the toilet or any other sewage drainage pipe. The fibers and resulting articles may also be aqueous responsive. The term aqueous responsive as used herein means that when placed in water or flushed, an observable and measurable change will result. Typical observations include noting that the article swells, pulls apart, dissolves, or observing a general weakened structure.

The nonwoven products produced from the fibers exhibit certain mechanical properties, particularly, strength, flexibility, softness, and absorbency. Measures of strength include dry and/or wet tensile strength. Flexibility is related to stiffness and can attribute to softness. Softness is generally described as a physiologically perceived attribute which is related to both flexibility and texture. Absorbency relates to the products' ability to take up fluids as well as the capacity to retain them.

Configuration of the Fibers

The fibers disclosed herein can also be splittable fibers. Rheological, thermal, and solidification differential behavior can potentially cause splitting. Splitting may also occur by a mechanical means such as ring rolling, stress or strain, use of an abrasive, or differential stretching, and/or by fluid induced distortion, such as hydrodynamic or aerodynamic.

For a bicomponent fiber, a composition as disclosed herein can be both the sheath and the core with one of the components containing more wax and/or additives than the other component. Alternatively, the composition disclosed herein can be the sheath with the core being some other materials, e.g., pure polymer. The composition can alternatively be the core with the sheath being some other polymer, e.g., pure polymer. The exact configuration of the fiber desired is dependent upon the use of the fiber.

Processes of Making the Compositions as Disclosed Herein

Melt mixing of the polymer and wax: The polymer and wax can be suitably mixed by melting the polymer in the presence of the wax. In the melt state, the polymer and wax are subjected to shear which enables a dispersion of the oil into the polymer. In the melt state, the wax and polymer are significantly more compatible with each other.

The melt mixing of the polymer and wax can be accomplished in a number of different processes, but processes with high shear are preferred to generate the preferred morphology of the composition. The processes can involve traditional thermoplastic polymer processing equipment. The general process order involves adding the polymer to the system, melting the polymer, and then adding the wax. However, the materials can be added in any order, depending on the nature of the specific mixing process.

Haake Batch Mixer: A Haake Batch mixer is a simple mixing system with low amount of shear and mixing. The unit is composed of two mixing screws contained within a heated, fixed volume chamber. The materials are added into the top of the unit as desired. The preferred order is to add the polymer, heat to 20° C. to 120° C. above the polymer's melting (or solidification) temperature into the chamber first. Once the polymer is melted, the wax can be added and mixed with the molten polymer once the wax melts. The mixture is then mixed in the melt with the two mixing screws for about 5 to about 15 minutes at screw RPM from about 60 to about 120. Once the composition is mixed, the front of the unit is removed and the mixed composition is removed in the molten state. By its design, this system leaves parts of the composition at elevated temperatures before crystallization starts for several minutes. This mixing process provides an intermediate quenching process, where the composition can take about 30 seconds to about 2 minutes to cool down and solidify. Mixture of polypropylene with hydrogenated soy bean oil in the Haake mixture shows that greater than 20 wt % of molten wax leads to incomplete incorporation of the wax in the polypropylene mixture, indicating that higher shear rates can lead to better incorporation of wax and greater amounts of wax able to be incorporated.

Single Screw Extruder: A single screw extruder is a typical process unit used in most molten polymer extrusion. The single screw extruder typically includes a single shaft within a barrel, the shaft and barrel engineered with certain screw elements (e.g., shapes and clearances) to adjust the shearing profile. A typical RPM range for single screw extruder is about 10 to about 120. The single screw extruder design is composed of a feed section, compression section and metering section. In the feed section, using fairly high void volume flights, the polymer is heated and supplied into the compression section, where the melting is completed and the fully molten polymer is sheared. In the compression section, the void volume between the flights is reduced. In the metering section, the polymer is subjected to its highest shearing amount using low void volume between flights. For this work, general purpose single screw designs were used. In this unit, a continuous or steady state type of process is achieved where the composition components are introduced at desired locations, and then subjected to temperatures and shear within target zones. The process can be considered to be a steady state process as the physical nature of the interaction at each location in the single screw process is constant as a function of time. This allows for optimization of the mixing process by enabling a zone-by-zone adjustment of the temperature and shear, where the shear can be changed through the screw elements and/or barrel design or screw speed.

The mixed composition exiting the single screw extruder can then be pelletized via extrusion of the melt into a liquid cooling medium, often water, and then the polymer strand can be cut into small pieces or pellets. Alternatively, the mixed composition can be used to produce the final formed structure, for example fibers. There are two basic types of molten polymer pelletization process used in polymer processing: strand cutting and underwater pelletization. In strand cutting the composition is rapidly quenched (generally much less than 10 seconds) in the liquid medium then cut into small pieces. In the underwater pelletization process, the molten polymer is cut into small pieces then simultaneously or immediately thereafter placed in the presence of a low temperature liquid which rapidly quenches and crystallizes the polymer. These methods are commonly known and used within the polymer processing industry.

The polymer strands that come from the extruder are rapidly placed into a water bath, most often having a temperature range of 1° C. to 50° C. (e.g., normally is about room temperature, which is 25° C.). An alternate end use for the mixed composition is further processing into the desired structure, for example fiber spinning, films or injection molding. The single screw extrusion process can provide for a high level of mixing and high quench rate. A single screw extruder also can be used to further process a pelletized composition into fibers and injection molded articles. For example, the fiber single screw extruder can be a 37 mm system with a standard general purpose screw profile and a 30:1 length to diameter ratio.

Twin Screw Extruder: A twin screw extruder is the typical unit used in most molten polymer extrusion, where high intensity mixing is required. The twin screw extruder includes two shafts and an outer barrel. A typical RPM range for twin screw extruder is about 10 to about 1200. The two shafts can be co-rotating or counter rotating and allow for close tolerance, high intensity mixing. In this type of unit, a continuous or steady state type of process is achieved where the composition components are introduced at desired locations along the screws, and subjected to high temperatures and shear within target zones. The process can be considered to be a steady state process as the physical nature of the interaction at each location in the single screw process is constant as a function of time. This allows for optimization of the mixing process by enabling a zone-by-zone adjustment of the temperature and shear, where the shear can be changed through the screw elements and/or barrel design.

The mixed composition at the end of the twin screw extruder can then be pelletized via extrusion of the melt into a liquid cooling medium, often water, and then the polymer strand is cut into small pieces or pellets. Alternatively, the mixed composition can be used to produce the final formed structure, for example fibers. There are two basic types of molten polymer pelletization process, strand cutting and underwater pelletization, used in polymer processing. In strand cutting the composition is rapidly quenched (generally much less than 10s) in the liquid medium then cut into small pieces. In the underwater pelletization process, the molten polymer is cut into small pieces then simultaneously or immediately thereafter placed in the presence of a low temperature liquid which rapidly quenches and crystallizes the polymer. An alternate end use for the mixed composition is direct further processing into filaments or fibers via spinning of the molten admixture accompanied by cooling.

Three different screw profiles can be employed using a Baker Perkins CT-25 25 mm corotating 40:1 length to diameter ratio system. This specific CT-25 is composed of nine zones where the temperature can be controlled, as well as the die temperature. Four liquid injection sites as also possible, located between zone 1 and 2 (location A), zone 2 and 3 (location B), zone 4 and 5 (location C). and zone 6 and 7 (location D).

The liquid injection location is not directly heated, but indirectly through the adjacent zone temperatures. Locations A, B, C and D can be used to inject the additive. Zone 6 can contain a side feeder for adding additional solids or used for venting. Zone 8 contains a vacuum for removing any residual vapor, as needed. Unless noted otherwise, the melted wax is injected at location A. The wax is melted via a glue tank and supplied to the twin-screw via a heated hose. Both the glue tank and the supply hose are heated to a temperature greater than the melting point of the wax (e.g., about 80° C.).

Two types of regions, conveyance and mixing, are used in the CT-25. In the conveyance region, the materials are heated (including through melting which is done in Zone 1 into Zone 2 if needed) and conveyed along the length of the barrel, under low to moderate shear. The mixing section contains special elements that dramatically increase shear and mixing. The length and location of the mixing sections can be changed as needed to increase or decrease shear as needed.

Two primary types of mixing elements are used for shearing and mixing. The first are kneading blocks and the second are thermal mechanical energy elements. The simple mixing screw has 10.6% of the total screw length using mixing elements composed of kneading blocks in a single set followed by a reversing element. The kneading elements are RKB 45/5/12 (right handed forward kneading block with 45° offset and five lobes at 12 mm total element length), followed by two RKB 45/5/36 (right handed forward kneading block with 45° offset and five lobes at 36 mm total element length), that is followed by two RKB 45/5/12 and reversing element 24/12 LH (left handed reversing element 24 mm pitch at 12 mm total element length).

The Simple mixing screw mixing elements are located in zone 7. The Intensive screw is composed of additional mixing sections, four in total. The first section is single set of kneading blocks is a single element of RKB45/5/36 (located in zone 2) followed by conveyance elements into zone 3 where the second mixing zone is located. In the second mixing zone, two RKB 45/5/36 elements are directly followed by four TME 22.5/12 (thermomechanical element with 22.5 teeth per revolution and total element length of 12 mm) then two conveyance elements into the third mixing area. The third mixing area, located at the end of zone 4 into zone 5, is composed of three RKB 45/5/36 and a KB45/5/12 LH (left handed forward reversing block with 45° offset and five lobes at 12 mm total element length. The material is conveyed through zone 6 into the final mixing area comprising two TME 22.5/12, seven RKB 45/5/12, followed by SE 24/12 LH. The SE 24/12 LH is a reversing element that enables the last mixing zone to be completely filled with polymer and additive, where the intensive mixing takes place. The reversing elements can control the residence time in a given mixing area and are a key contributor to the level of mixing.

The High Intensity mixing screw is composed of three mixing sections. The first mixing section is located in zone 3 and is two RKB45/5/36 followed by three TME 22.5/12 and then conveyance into the second mixing section. Prior to the second mixing section three RSE 16/16 (right handed conveyance element with 16 mm pitch and 16 mm total element length) elements are used to increase pumping into the second mixing region. The second mixing region, located in zone 5, is composed of three RKB 45/5/36 followed by a KB 45/5/12 LH and then a full reversing element SE 24/12 LH. The combination of the SE 16/16 elements in front of the mixing zone and two reversing elements greatly increases the shear and mixing. The third mixing zone is located in zone 7 and is composed of three RKB 45/5/12, followed by two TME 22.5.12 and then three more RKB45/5/12. The third mixing zone is completed with a reversing element SE 24/12 LH.

An additional screw element type is a reversing element, which can increase the filling level in that part of the screw and provide better mixing. Twin screw compounding is a mature field. One skilled in the art can consult books for proper mixing and dispersion. These types of screw extruders are well understood in the art and a general description can be found in: Twin Screw Extrusion 2E: Technology and Principles by James White from Hansen Publications. Although specific examples are given for mixing, many different combinations are possible using various element configurations to achieve the needed level of mixing.

Properties of Compositions

The compositions as disclosed herein can have one or more of the following properties that provide an advantage over known thermoplastic compositions. These benefits can be present alone or in a combination.

Shear Viscosity Reduction: As shown in FIG. 1, addition of the wax, e.g., HSBO, to the thermoplastic polymer, e.g., Basell PH-835, reduces the viscosity of the thermoplastic polymer (here, polypropylene in the presence of the molten HSBO wax). Viscosity reduction is a process improvement as it can allow for effectively higher polymer flow rates by having a reduced process pressure (lower shear viscosity), or can allow for an increase in polymer molecular weight, which improves the material strength. Without the presence of the wax, it may not be possible to process the polymer with a high polymer flow rate at existing process conditions in a suitable way.

Sustainable Content: Inclusion of sustainable materials into the existing polymeric system is a strongly desired property. Materials that can be replaced every year through natural growth cycles contribute to overall lower environmental impact and are desired.

Pigmentation: Adding pigments to polymers often involves using expensive inorganic compounds that are particles within the polymer matrix. These particles are often large and can interfere in the processing of the composition. Using a wax as disclosed herein, because of the fine dispersion (as measured by droplet size) and uniform distribution throughout the thermoplastic polymer allows for coloration, such as via traditional ink compounds. Soy ink is widely used in paper publication) that does not impact processability.

Fragrance: Because the waxes, for example HSBO, can contain perfumes much more preferentially than the base thermoplastic polymer, the present composition can be used to contain scents that are beneficial for end-use. Many scented candles are made using SBO based or paraffin based materials, so incorporation of these into the polymer for the final composition is useful.

Surface Feel: The presence of the wax can change the surface properties of the composition, compared to a thermoplastic polymer composition without a wax, making it feel softer.

Figure 2:
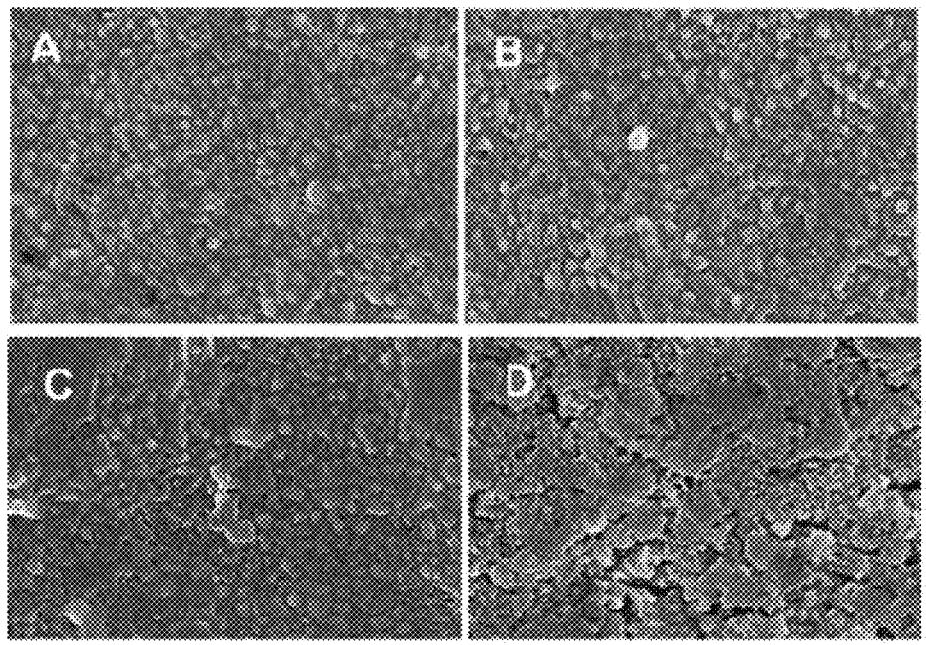
FIG. 2 shows scanning electron microscopy (SEM) images of unmodified polypropylene (A) and Examples 1-3 (B-D), compositions as disclosed herein.

Morphology: The benefits are delivered via the morphology produced in production of the compositions. The morphology is produced by a combination of intensive mixing and rapid crystallization. The intensive mixing comes from the compounding process used and rapid crystallization comes from the cooling process used. High intensity mixing is desired and rapid crystallization is used to preserves the fine pore size and relatively uniform pore size distribution. FIG. 2 shows HSBO in Basell Profax PH-835, with the small pore sizes of less than 10 μm, less than 5 μm, and less than 1 μm.

Improved Spinning Performance: Adding the wax has shown to improve spinning of fibers, enabling a finer diameter filament to be achieved vs the neat polymer the additive has been admixed into during composition preparation.

Processes for Making Fibers

Fibers can be spun from a melt of the compositions as disclosed herein. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Spinning can occur at 120° C. to about 320° C., preferably 185° C. to about 250° C. and most preferably from 200° C. to 230° C. Fiber spinning speeds of greater than 100 meters/minute are preferred. Preferably, the fiber spinning speed is about 1,000 to about 10,000 meters/minute, more preferably about 2,000 to about 7,000 meters/minute, and most preferably about 2,500 to about 5,000 meters/minute. The polymer composition is spun fast to avoid brittleness in the fiber.

Continuous filaments or fibers can be produced through spunbond methods. Essentially continuous or essentially discontinuous filaments or fibers can be produced through melt fibrillation methods such as meltblowing or melt film fibrillation processes. Alternatively, non-continuous (staple fibers) fibers can be produced. The various methods of fiber manufacturing can also be combined to produce a combination technique.

The homogeneous blend can be melt spun into monocomponent or multicomponent fibers on conventional melt spinning equipment. The equipment will be chosen based on the desired configuration of the multicomponent. Commercially available melt spinning equipment is available from Hills, Inc. located in Melbourne, Fla. The temperature for spinning is about 100° C. to about 320° C. The processing temperature is determined by the chemical nature, molecular weights and concentration of each component. The fibers spun can be collected using conventional godet winding systems or through air drag attenuation devices. If the godet system is used, the fibers can be further oriented through post extrusion drawing at temperatures of about 25° C. to about 200° C. The drawn fibers may then be crimped and/or cut to form non-continuous fibers (staple fibers) used in a carding, airlaid, or fluidlaid process.

For example, a suitable process for spinning bicomponent sheath core fibers using the composition in the sheath and a different composition in the core is as follows. A composition is first prepared through compounding containing 10 wt % HSBO and a second composition is first prepared through compounding containing 30 wt % HSBO. The 10 wt % HSBO component extruder profile may be 180° C., 200° C. and 220° C. in the first three zones of a three heater zone extruder. The transfer lines and melt pump heater temperatures may be 220° C. for the first composition. The second composition extruder temperature profile can be 180° C., 230° C. and 230° C. in the first three zones of a three heater zone extruder. The transfer lines and melt pump can be heated to 230° C. In this case, the spinneret temperature can be 220° C. to 230° C.

Fine Fiber Production

In one embodiment, the homogenous blend is spun into one or more filaments or fibers by melt film fibrillation. Suitable systems and melt film fibrillation methods are described in U.S. Pat. Nos. 6,315,806, 5,183,670, and 4,536,361, to Torobin et al., and U.S. Pat. Nos. 6,382,526, 6,520,425, and 6,695,992, to Reneker et al. and assigned to the University of Akron. Other melt film fibrillation methods and systems are described in the U.S. Pat. Nos. 7,666,343 and 7,931,457, to Johnson, et al., U.S. Pat. No. 7,628,941, to Krause et al., and U.S. Pat. No. 7,722,347, to Krause, et al. Methods and apparatus described in above patents provide nonwoven webs with uniform and narrow fiber distribution, reduced or minimal fiber defects. Melt film fibrillation process comprises providing one or more melt films of the homogenous blend, one or more pressurized fluid streams (or fiberizing fluid streams) to fibrillate the melt film into ligaments, which are attenuated by the pressurized fluid stream. Optionally, one or more pressurized fluid streams may be provided to aid the attenuation and quenching of the ligaments to form fibers. Fibers produced from the melt film fibrillation process using one of embodiment homogenous blend would have diameters typically ranging from about 100 nanometer (0.1 micrometer) to about 5000 nanometer (5 micrometer). In one embodiment, the fibers produced from the melt film fibrillation process of the homogenous blend would be less than 2 micrometer, more preferably less than 1 micrometer (1000 nanometer), and most preferably in the range of 100 nanometer (0.1 micrometer) to about 900 nanometer (0.9 micrometer). The average diameter (an arithmetic average diameter of at least 100 fiber samples) of fibers of the homogenous blend produced using the melt film fibrillation would be less than 2.5 micrometer, more preferably less than 1 micrometer, and most preferably less than 0.7 micrometer (700 nanometer). The median fiber diameter can be 1 micrometer or less. In an embodiment, at least 50% of the fibers of the homogenous blend produced by the melt film fibrillation process may have diameter less than 1 micrometer, more preferably, at least 70% of the fibers may have diameter less than 1 micrometer, and most preferably, at least 90% of the fibers may have diameter less than 1 micrometer. In certain embodiments, even 99% or more fibers may have diameter less than 1 micrometer when produced using the melt film fibrillation process.

In the melt film fibrillation process, the homogenous blend is typically heated until it forms a liquid and flows easily. The homogenous blend may be at a temperature of from about 120° C. to about 350° C. at the time of melt film fibrillation, in one embodiment from about 160° C. to about 350° C., and in another embodiment from about 200° C. to about 300° C. The temperature of the homogenous blend depends on the composition. The heated homogenous blend is at a pressure from about 15 pounds per square inch absolute (psia) to about 400 psia, in another embodiment from about 20 psia to about 200 psia, and in yet another embodiment from about 25 psia to about 100 psia.

Non-limiting examples of the pressurized fiberizing fluid stream are gases such as air or nitrogen or any other fluid compatible (defined as reactive or inert) with homogenous blend composition. The fiberizing fluid stream can be at a temperature close to the temperature of the heated homogenous blend. The fiberizing fluid stream temperature may be at a higher temperature than the heated homogenous blend to help in the flow of the homogenous blend and the formation of the melt film. In one embodiment, the fiberizing fluid stream temperature is about 100° C. above the heated homogenous blend, in another embodiment about 50° C. above the heated homogenous blend, or just at temperature of the heated homogenous blend. Alternatively, the fiberizing fluid stream temperature can be below the heated homogenous blend temperature. In one embodiment, the fiberizing fluid stream temperature is about 50° C. below the heated homogenous blend, in another embodiment about 100° C. below the heated homogenous blend, or 200° C. below heated homogenous blend. In certain embodiments, the temperature of the fiberizing fluid stream may be ranging from about −100° C. to about 450° C., more preferably, ranging from about −50° C. to 350° C., and most preferably, ranging from about 0° C. to about 300° C. The pressure of the fiberizing fluid stream is sufficient to fibrillate the homogenous blend into fibers, and is above the pressure of the heated homogenous blend. The pressure of the fiberizing fluid stream may range from about 15 psia to about 500 psia, more preferably from about 30 psia to about 200 psia, and most preferably from about 40 psia to about 100 psia. The fiberizing fluid stream may have a velocity of more than about 200 meter per second at the location of melt film fibrillation. In one embodiment, at the location of melt film fibrillation, the fiberizing fluid stream velocity will be more than about 300 meter per second, i.e., transonic velocity; in another embodiment more than about 330 meter per second, i.e., sonic velocity; and in yet another embodiment from about 350 to about 900 meters per second (m/s), i.e., supersonic velocity from about Mach 1 to Mach 3. The fiberizing fluid stream may pulsate or may be a steady flow. The homogenous blend throughput will primarily depend upon the specific homogenous blend used, the apparatus design, and the temperature and pressure of the homogenous blend. The homogenous blend throughput will be more than about 1 gram per minute per orifice, for example in a circular nozzle. In one embodiment, the homogenous blend throughput will be more than about 10 gram per minute per orifice and in another embodiment greater than about 20 gram per minute per orifice, and in yet another embodiment greater than about 30 gram per minute per orifice. In an embodiment with the slot nozzle, the homogenous blend throughput will be more than about 0.5 kilogram per hour per meter width of the slot nozzle. In another slot nozzle embodiment, the homogenous blend throughput will be more than about 5 kilogram per hour per meter width of the slot nozzle, and in another slot nozzle embodiment, the homogenous blend throughput will be more than about 20 kilogram per hour per meter width of the slot nozzle, and in yet another slot nozzle embodiment, the homogenous blend throughput will be more than about 40 kilogram per hour per meter width of the slot nozzle. In certain embodiments of the slot nozzle, the homogenous blend throughput may exceed about 60 kilogram per hour per meter width of the slot nozzle. There will likely be several orifices or nozzles operating at one time which further increases the total production throughput. The throughput, along with pressure, temperature, and velocity, are measured at the orifice or nozzle for both circular and slot nozzles.

Optionally, an entraining fluid can be used to induce a pulsating or fluctuating pressure field to help in forming fibers. Non-limiting examples of the entraining fluid are pressurized gas stream such as compressed air, nitrogen, oxygen, or any other fluid compatible (defined as reactive or inert) with the homogenous blend composition. The entertaining fluid with a high velocity can have a velocity near sonic speed (i.e. about 330 m/s) or supersonic speeds (i.e. greater than about 330 m/s). An entraining fluid with a low velocity will typically have a velocity of from about 1 to about 100 m/s and in another embodiment from about 3 to about 50 m/s. It is desirable to have low turbulence in the entraining fluid stream 14 to minimize fiber-to-fiber entanglements, which usually occur due to high turbulence present in the fluid stream. The temperature of the entraining fluid 14 can be the same as the above fiberizing fluid stream, or a higher temperature to aid quenching of filaments, and ranges from about −40° C. to 40° C. and in another embodiment from about 0° C. to about 25° C. The additional fluid stream may form a "curtain" or "shroud" around the filaments exiting from the nozzle. Any fluid stream may contribute to the fiberization of the homogenous blend and can thus generally be called fiberizing fluid stream.

The spunlaid processes disclosed herein use a high speed spinning process as disclosed in U.S. Pat. Nos. 3,802,817; 5,545,371; 6,548,431 and 5,885,909. In these melt spinning processes, extruders supply molten polymer to melt pumps, which deliver specific volumes of molten polymer that transfer through a spinpack, composed of a multiplicity of capillaries formed into fibers, where the fibers are cooled through an air quenching zone and are pneumatically drawn down to reduce their size into highly attenuated fibers to increase fiber strength through molecular level fiber orientation. The drawn fibers are then deposited onto a porous belt, often referred to as a forming belt or forming table.

Spunlaid Process

The fibers forming the base substrate disclosed herein are preferably continuous filaments forming spunlaid fabrics. Spunlaid fabrics are defined as unbonded fabrics having basically no cohesive tensile properties formed from essentially continuous filaments. Continuous filaments are defined as fibers with high length to diameter ratios, with a ratio of more than 10,000:1. Continuous filaments that compose the spunlaid fabric are not staple fibers, short cut fibers or other intentionally made short length fibers. The continuous filaments, defined as essentially continuous, are on average, more than 100 mm long, preferably more than 200 mm long. The continuous filaments are also not crimped, intentionally or unintentionally. Essentially discontinuous fibers and filaments are defined as having a length less than 100 mm long, preferably less than 50 mm long.

The spunlaid processes can use a high speed spinning process as disclosed in U.S. Pat. Nos. 3,802,817; 5,545,371; 6,548,431 and 5,885,909. In these melt spinning processes, extruders supply molten polymer to melt pumps, which deliver specific volumes of molten polymer that transfer through a spinpack, composed of a multiplicity of capillaries formed into fibers, where the fibers are cooled through an air quenching zone and are pneumatically drawn down to reduce their size into highly attenuated fibers to increase fiber strength through molecular level fiber orientation. The drawn fibers are then deposited onto a porous belt, often referred to as a forming belt or forming table.

In one embodiment, the spunlaid process used to make the continuous filaments will contain 100 to 10,000 capillaries per meter, preferably 200 to 7,000 capillaries per meter, more preferably 500 to 5,000 capillaries per meter. The polymer mass flow rate per capillary in the present invention will be greater than 0.3 GHM (grams per hole per minute). The preferred range is from 0.35 GHM to 2 GHM, preferably between 0.4 GHM and 1 GHM, still more preferred between 0.45 GHM and 8 GHM and the most preferred range from 0.5 GHM to 0.6 GHM.

The spunlaid process can contain a single process step for making the highly attenuated, uncrimped continuous filaments. Extruded filaments are drawn through a zone of quench air where they are cooled and solidified as they are attenuated. Such spunlaid processes are disclosed in U.S. Pat. No. 3,338,992, U.S. Pat. No. 3,802,817, U.S. Pat. No. 4,233,014 US 5,688,468, U.S. Pat. No. 6,548,431 B1, U.S. Pat. No. 6,908,292 B2 and U.S. Application 2007/0057414A1. The technology described in EP 1,340,843 B1 and EP 1 323,852 B1 can also be used to produce the spunlaid nonwovens. The highly attenuated continuous filaments are directly drawn down from the exit of the polymer from the spinneret to the attenuation device, wherein the continuous filament diameter or denier does not change substantially as the spunlaid fabric is formed on the forming table Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof, as well as the other mixture disclosed herein. Other suitable polymeric materials include thermoplastic starch compositions as described in detail in U.S. publications 2003/0109605A1 and 2003/0091803. Still other suitable polymeric materials include ethylene acrylic acid, polyolefin carboxylic acid copolymers, and combinations thereof. The polymers described in U.S. Pat. No. 6,746,766, U.S. Pat. No. 6,818,295, U.S. Pat. No. 6,946,506 and US Published Application 03/0092343. Common thermoplastic polymer fiber grade materials are preferred, most notably polyester based resins, polypropylene based resins, polylactic acid based resin, polyhydroxyalkonoate based resin, and polyethylene based resin and combination thereof. Most preferred are polyester and polypropylene based resins.

It should also be noted that the ability to utilize mixture compositions above 40 weigh percent (wt %) wax in the extrusion process, where the masterbatch level of wax is combined with a lower concentration (down to 0 wt %) thermoplastic composition during extrusion to produce a wax content within the target range.

In the process of spinning fibers, particularly as the temperature is increased above 105° C., typically it is desirable for residual water levels to be 1%, by weight of the fiber, or less, alternately 0.5% or less, or 0.15% or less.

Articles

The fibers can be converted to nonwovens by different bonding methods. Continuous fibers can be formed into a web using industry standard spunbond type technologies while staple fibers can be formed into a web using industry standard carding, airlaid, or wetlaid technologies. Typical bonding methods include: calender (pressure and heat), thru-air heat, mechanical entanglement, hydrodynamic entanglement, needle punching, and chemical bonding and/or resin bonding. The calender, thru-air heat, and chemical bonding are the preferred bonding methods for the starch polymer fibers. Thermally bondable fibers are required for the pressurized heat and thru-air heat bonding methods.

The fibers that are made with any of the compositions discussed herein may also be bonded or combined with other synthetic or natural fibers to make disposable articles. The synthetic or natural fibers may be blended together in the forming process or used in discrete layers. Suitable synthetic fibers include fibers made from polypropylene, polyethylene, polyester, polyacrylates, and copolymers thereof and mixtures thereof. Natural fibers include cellulosic fibers and derivatives thereof. Suitable cellulosic fibers include those derived from any tree or vegetation, including hardwood fibers, softwood fibers, hemp, and cotton. Also included are fibers made from processed natural cellulosic resources such as rayon.

Figure 3:
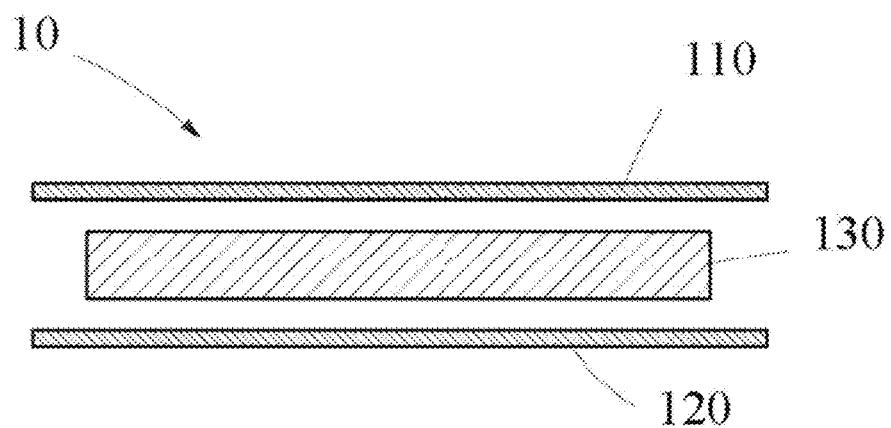
FIG. 3 is a schematic representation of a disposable absorbent article.

The fibers that are made with any of the compositions discussed herein may be used to make one or more layers of nonwoven that can then be used to make a disposable article. The nonwoven described herein may be combined with additional nonwovens or films to produce a laminate used either by itself or as a component in a complex combination of other materials, such as a baby diaper or feminine care pad. Disposable articles that may benefit from the use of the fibers and nonwovens described herein include disposable absorbent articles such as baby diapers, training pants, adult incontinence articles, panty liners, sanitary napkins, tampons, absorbent pads (such as the SWIFFER WET and SWIFFER WETJET pads). A typical absorbent article that may include at least one layer of a nonwoven comprising fibers that are made with any of the compositions discussed herein is schematically represented in FIG. 3. The disposable absorbent article 10 includes a liquid pervious layer 110, a liquid impervious layer 210 and an absorbent core 310 disposed between the liquid pervious and impervious layers. In one embodiment, fibers that are made with any of the compositions discussed herein are included (preferably in the form of a nonwoven layer) in at least one of the liquid pervious layer, the liquid impervious layer, and the absorbent core of a disposable absorbent article. In another embodiment, fibers that are made with any of the compositions discussed herein are included in at least one of the layers that form a cleaning wipe suitable to cleaning soft or hard surfaces. Other disposable articles include filters for air, oil and water; vacuum cleaner filters; furnace filters; face masks; coffee filters, tea or coffee bags; thermal insulation materials and sound insulation materials. The fibrous web may also include odor absorbents, termite repellants, insecticides, rodenticides, and the like, for specific uses. The resultant product absorbs water and oil and may find use in oil or water spill clean-up, or controlled water retention and release for agricultural or horticultural applications. The resultant fibers or fiber webs may also be incorporated into other materials such as saw dust, wood pulp, plastics, and concrete, to form composite materials, which can be used as building materials such as walls, support beams, pressed boards, dry walls and backings, and ceiling tiles; other medical uses such as casts, splints, and tongue depressors; and in fireplace logs for decorative and/or burning purpose.

EXAMPLES

Polymers: The primary polymers used in this work are polypropylene (PP) and polyethylene (PE), but other polymers can be used (see, e.g., U.S. Pat. No. 6,783,854, which provides a comprehensive list of polymers that are possible, although not all have been tested). Specific polymers evaluated were:

Basell Profax PH-835: Produced by Lyondell-Basell as nominally a 35 melt flow rate Ziegler-Natta isotactic polypropylene.

Exxon Achieve 3854: Produced by Exxon-Mobil Chemical as nominally a 25 melt flow rate metallocene isotactic polypropylene.

Total 8650: Produced by Total Chemicals as a nominally 10 melt flow rate Ziegler-Natta isotactic ethylene random copolymer polypropylene.

Danimer 27510: Proprietary polyhydroxyalkanoate copolymer.

Dow Aspun 6811A: Produced by Dow Chemical as a 27 melt index polyethylene copolymer.

BASF Ultramid B27: Produced by BASF as a low viscosity polyamide-6 resin.

Eastman 9921: Produced by Eastman Chemical as a copolyester terephthalic homopolymer with a nominally 0.81 intrinsic viscosity.

Natureworks Ingeo Biopolymer 4032D: Produced by Natureworks as polylactic acid polymer.

Waxes: Specific examples used were: Hydrogenated Soy Bean Oil (HSBO); Partially Hydrogenated Soy Bean Oil (HSBO); Partially Hydrogenated Palm Kernel Oil (PK-PKO); a commercial grade soy bean oil based-wax candle with pigmentation and fragrance; standard green Soy Bean Green Ink Pigment Compositions were made using a Baker Perkins CT-25 Screw, with the zones set as noted in Table 1. Table 1 is shown in FIGS. 4-6.

Examples 1-26 and 42-46 were made using polypropylene resins, while examples 27-41 were made using other types of thermoplastic polymer resins. All examples successfully formed pellets, except examples 34, 37 and 44. A slight excess of the wax was noted for examples 9, 12, and 27, e.g., small amounts of surging were noted at the outlet of the twin-screw, but not sufficient to break the strand and disrupt the process. The slight excess of wax indicates that the level of mixing is insufficient at that level or the polymer/wax composition is close to saturation. Examples 43 and 44 also included an added pigment and perfume to the wax.

Examples 1-46 show the polymer plus additive tested in a stable range and to the limit. As used herein, stable refers to the ability of the composition to be extruded and to be pelletized. What was observed was that during the stable composition, strands from the B&P 25 mm system could be extruded, quenched in a water bath at 5° C. and cut via a pelletizer without interruption. The twin-screw extrudate was immediately dropped into the water bath.

During stable extrusion, no significant amount of wax separated from the formulation strand (>99 wt % made it through the pelletizer). Saturation of the composition can be noted by separation of the polymer and wax from each other at the end of the twin-screw. The saturation point of the wax in the composition can change based on the wax and polymer combination, along with the process conditions. The practical utility is that the wax and polymer remain admixed and do not separate, which is a function of the mixing level and quench rate for proper dispersion of the additive. Specific Examples where the extrusion became unstable from high wax inclusion are Example 34, 37, and 41.

Example 42 was processed using 30 wt % HSBO plus the addition of a scent and pigment (e.g., Febreze Rosewood scent and pigmented candle). One candle was added per 20 lb of wax into the glue tank and stirred manually. The candle wick was removed before addition. The candle contained both a pigment and perfume that were present in the as-formed pellets of the composition at the end of the process. Example 43 was identical to Example 42 except the vacuum was turned on to determine how much perfume or volatiles could be removed. No difference between as-formed pellets of Example 42 and Example 43 could be observed.

Examples 1-45 show the polymer plus additive tested in a stable range and to the limit. As used herein, stable refers to the ability of the composition to be extruded and to be pelletized. What was observed was that during the stable composition, strands from the B&P 25 mm system could be extruded, quenched in a water bath at 5° C. and cut via a pelletizer without interruption. The twin-screw extrudate was immediately dropped into the water bath. During stable extrusion, no significant amount of oil separated from the formulation strand (>99 wt % made it through the pelletizer). The composition became unstable when it was clear that the polymer and oil were separating from each other at the end of the twin-screw and the composition strands could not be maintained. Without being bound by theory, the polymer at this point is considered fully saturated. The saturation point can change based on the oil and polymer combination, along with the process conditions. The practical utility is that the oil and polymer remain admixed and do not separate, which is a function of the mixing level and quench rate for proper dispersion of the additive. Specific Examples where the extrusion became unstable from high oil inclusion are Example 5, 7, 10, 12, 16 and 42.

Fibers can be produced by melt spinning a composition of any one of Examples 1-45. Fibers were melt spun with several spinning examples.

The specific melt spinning equipment was a specially designed bicomponent extrusion system that consists of two single extruders, followed by a melt pump after each extruder. The two melt streams are combined into a sheath/core spinpack purchased from Hills Inc. The spinpack had 144 holes with capillary orifice diameter of 0.35 mm. The fibers extruded through the spinpack were quenched on two sides using a 1m long quench system that blows air. The fibers are attenuated using a high pressure aspirator that draws the filaments down. The as-spun fibers were deposited onto a belt and collected to measure the final as-spun filament diameter. The as-spun filament diameter is an average of 10 measurements made under a light microscope. The reported fiber diameter is the minimum fiber diameter that could be achieved without any filament breaks over five minutes for the entire 144 filaments being extruded. The mass throughput used was 0.5 grams per capillary per minute (ghm). The specific fibers made and the processes for making them are shown in Table 2. Table 2 is shown in FIGS. 7 and 8.

Examples 47-65 show the results from producing useful fibers and the benefit of improved spinnability by adding wax. The examples show that utilizing polypropylene with wax in the core or into the sheath and core improve the spinnability and enable finer filaments to be produced. Finer fibers can improve softness, barrier properties and wicking behavior.

Spunbond nonwovens were made by using the porous collection belt and adjusting the belt speed to target 20 grams per square meter (gsm). The collected fibers were first passed through a heated press roll at 100° C. at 50 PLI (pounds per linear inch) and then a heated calendering system for the final thermal point bonding, followed by winding the continuous spunbond nonwoven onto a roll for later property measurements. The heated calendering system consisted of a heated engraved roll and heated smooth roll. The heated engraved roll had 18% raised bonding area. The calender roll pressure was held constant at 350 PLI and the line speed of the forming belt was held constant at 38 meters per minute.

The tensile properties of base substrates and structured substrates were all measured the same way. The gauge width is 50 mm, gauge length is 100 mm in the MD and 50 mm in the CD and the extension rate is 100 mm/min. The values reported are for strength and elongation at peak, unless stated otherwise. Separate measurements are made for the MD and CD properties. The typical units are Newton (N), and they are Newtons per centimeter (N/cm). The values presented are the average of at least ten measurements. The perforce load is 0.2 N. The samples should be stored at 23±2° C. and at 50±2% relative humidity for 24 hours with no compression, then tested at 23±2° C. and at 50±2%. The tensile strength as reported here is the peak tensile strength in the stress-strain curve. The elongation at tensile peak is the percent elongation at which the tensile peak is recorded.

Examples 66-105 show that useful spunbond nonwovens can be produced. The specifics of Examples 64-103 are shown in Table 3. Table 3 is shown in FIGS. 9 ad 10. The examples show that an optimum bonding temperature is to achieve at a particular fiber composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A material web comprising:
   a. a first fiber layer comprising a plurality of fibers, each of which comprising an intimate admixture of a thermoplastic polymer, and a wax and/or oil, wherein at least some of the wax and/or oil is exposed at an outer surface of the fibers, the first fiber layer having a first surface energy; and
   b. a second layer that is adjacent to the first fiber layer, the second layer comprising a second surface energy, wherein the first surface energy is higher than the second surface energy,
   wherein the plurality of fibers comprise bicomponent fibers comprising a first component and a second component, and wherein the wax or oil concentration in the first component is different than the concentration of the wax or oil in the second component.

2. The material web of claim 1, wherein the bicomponent fibers are arranged in a side-by-side configuration.

3. The material web of claim 1, wherein the bicomponent fibers are arranged in a core-sheath configuration.

4. The material web of claim 1, wherein the material web comprises fine fibers having a diameter of from 0.1 microns to about 5 microns.

5. The material web of claim 1, wherein the wax and/or oil comprises a stearic acid.

6. The material web of claim 1, wherein the wax and/or oil comprises a triglyceride.

7. The material web of claim 1, wherein the the material web comprises a plurality of carded staple length crimped fibers.

8. The material web of claim 1, wherein the material web comprises a plurality of spunbond crimped fibers.

9. The material web of claim 1, wherein the second layer comprises a film.

10. The material web of claim 1, wherein the film comprises a surfactant.

11. The material web of claim 1, wherein the second layer comprises a plurality of fibers and wherein the plurality of fibers of the second layer comprise cellulosic fibers.

12. The material web of claim 11, wherein the cellulosic fibers comprise rayon fibers.

13. The material web of claim 12, wherein the material web comprises mechanical entanglement, hydrodynamic entanglement, or needle punching.

14. The material web of claim 1, further comprising an additive associated with the wax and/or oil.

15. The material web of claim 14, wherein the additive is a perfume or a colorant.

16. The material web of claim 1, wherein the plurality of fibers of the first fiber layer are crimped.

17. The material web of claim 16, wherein the plurality of fibers of the first fiber layer are bicomponent fibers having a first component and a second component, wherein the first component is different than the second component such that the difference in crystallinity causes crimping.

18. The material web of claim 17, wherein the plurality of fibers of the first fiber layer are spunbond.

19. The material web of claim 17, wherein the plurality of fibers of the first fiber layer are carded.

* * * * *